(12) United States Patent
Murakami

(10) Patent No.: US 10,458,927 B2
(45) Date of Patent: Oct. 29, 2019

(54) IMAGE PROCESSING DEVICE, IMAGE PROCESSING METHOD, AND PROGRAM

(71) Applicant: FUJIFILM Corporation, Tokyo (JP)

(72) Inventor: Osamu Murakami, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 25 days.

(21) Appl. No.: 15/788,033

(22) Filed: Oct. 19, 2017

(65) Prior Publication Data

US 2018/0052120 A1 Feb. 22, 2018

Related U.S. Application Data

(63) Continuation of application No. PCT/JP2016/057052, filed on Mar. 8, 2016.

(30) Foreign Application Priority Data

Apr. 30, 2015 (JP) .................................. 2015-093216

(51) Int. Cl.
*G01N 23/04* (2018.01)
*G01N 23/18* (2018.01)
(Continued)

(52) U.S. Cl.
CPC ............. *G01N 23/04* (2013.01); *G01N 23/18* (2013.01); *G06T 3/40* (2013.01); *G06T 5/50* (2013.01);
(Continued)

(58) Field of Classification Search
CPC ........................................................ G06T 5/50
See application file for complete search history.

(56) References Cited

U.S. PATENT DOCUMENTS 5,359,513 A * 10/1994 Kano .................... G06T 3/0081
128/922
5,434,903 A * 7/1995 Hoornaert ............ A61B 6/4441
378/101
(Continued)

FOREIGN PATENT DOCUMENTS

JP 03-137548 A 6/1991
JP 03-209583 A 9/1991
(Continued)

OTHER PUBLICATIONS

International Preliminary Report on Patentability issued from the International Bureau in counterpart International Application No. PCT/JP2016/057052, dated Jan. 18, 2017.
(Continued)

*Primary Examiner* — Jitesh Patel
(74) *Attorney, Agent, or Firm* — Sughrue Mion, PLLC

(57) ABSTRACT

A radiation image obtained by imaging a test object irradiated with radiation is acquired. A standard image which is a normal radiation image of the test object imaged under the same imaging condition as in the acquired radiation image is stored in a standard image storage unit. Differential values of pixel values between corresponding pixels of the radiation image acquired by the radiation image acquisition unit and the standard image stored in the standard image storage unit are detected. A differential region between the radiation image and the standard image so that positive and negative of the differential values in the differential region can be determined on the basis of a detection result of the differential value detection unit is displayed on a display unit.

21 Claims, 16 Drawing Sheets

(51) Int. Cl.
  *G06T 3/40* (2006.01)
  *G06T 5/50* (2006.01)
  *G06T 11/60* (2006.01)
  *G06T 7/00* (2017.01)
  *G06T 11/00* (2006.01)

(52) U.S. Cl.
  CPC ............ *G06T 7/001* (2013.01); *G06T 11/001* (2013.01); *G06T 11/008* (2013.01); *G06T 11/60* (2013.01); *G01N 2223/401* (2013.01); *G01N 2223/408* (2013.01); *G01N 2223/646* (2013.01); *G06T 2207/10116* (2013.01); *G06T 2207/30164* (2013.01)

(56) References Cited

U.S. PATENT DOCUMENTS

| | | | | |
|---|---|---|---|---|
| 5,623,560 | A * | 4/1997 | Nakajima | G06K 9/6203 382/295 |
| 5,828,775 | A * | 10/1998 | Takeo | G06T 5/009 382/132 |
| 2001/0038707 | A1 | 11/2001 | Ohara | |
| 2002/0106123 | A1 * | 8/2002 | Inoue | G06T 5/009 382/168 |
| 2004/0081342 | A1 * | 4/2004 | Sato | G06T 5/50 382/128 |
| 2005/0213801 | A1 | 9/2005 | Ohara | |
| 2007/0222464 | A1 | 9/2007 | Honda et al. | |
| 2008/0287784 | A1 * | 11/2008 | Ohta | A61B 6/481 600/431 |
| 2011/0313479 | A1 * | 12/2011 | Rubin | A61B 6/5235 607/1 |
| 2012/0069957 | A1 * | 3/2012 | Nakayama | A61B 6/022 378/21 |
| 2012/0233542 | A1 | 9/2012 | Funakoshi | |
| 2014/0285689 | A1 * | 9/2014 | Ryu | H04N 5/357 348/241 |
| 2014/0291515 | A1 | 10/2014 | Tajima et al. | |

FOREIGN PATENT DOCUMENTS

| | | |
|---|---|---|
| JP | 08-146137 A | 6/1996 |
| JP | 09-166555 A | 6/1997 |
| JP | 09-166556 A | 6/1997 |
| JP | 2001-299733 A | 10/2001 |
| JP | 2003-323861 A | 11/2003 |
| JP | 2004-209152 A | 7/2004 |
| JP | 2006-352170 A | 12/2006 |
| JP | 2007-256125 A | 10/2007 |
| JP | 2011-061047 A | 3/2011 |
| JP | 2012-019220 A | 1/2012 |
| JP | 2012-088291 A | 5/2012 |
| JP | 4988482 B2 | 8/2012 |
| JP | 2014-182064 A | 9/2014 |

OTHER PUBLICATIONS

International Search Report dated May 31, 2016, issued by the International Bureau in counterpart Application No. PCT/JP2016/057052.

Written Opinion dated May 31, 2016, issued by the International Bureau in counterpart Application No. PCT/JP2016/057052.

* cited by examiner

FIG. 3
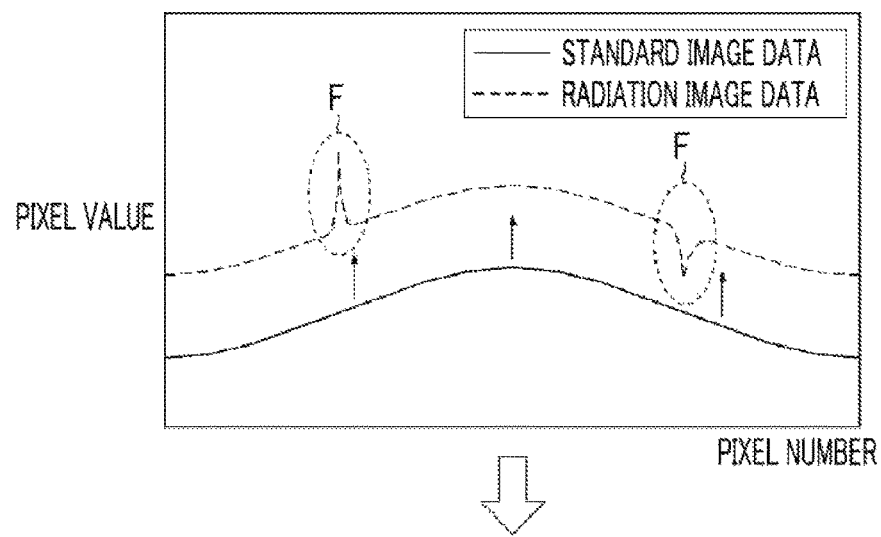
(a)
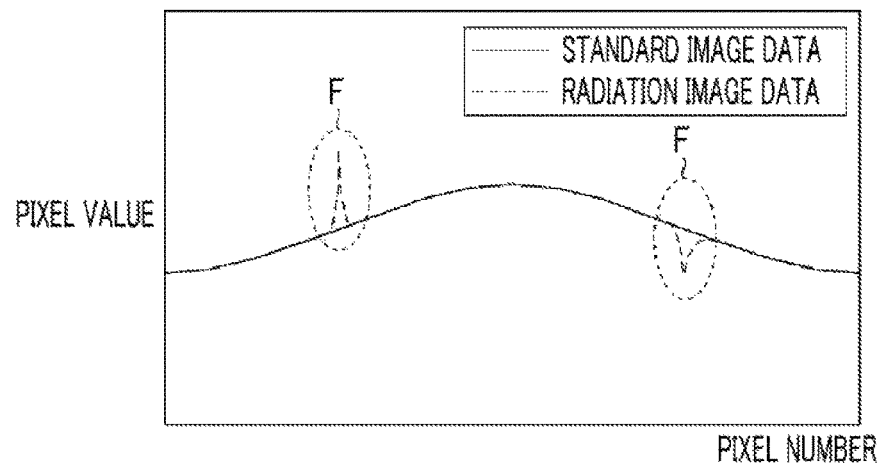
(b)

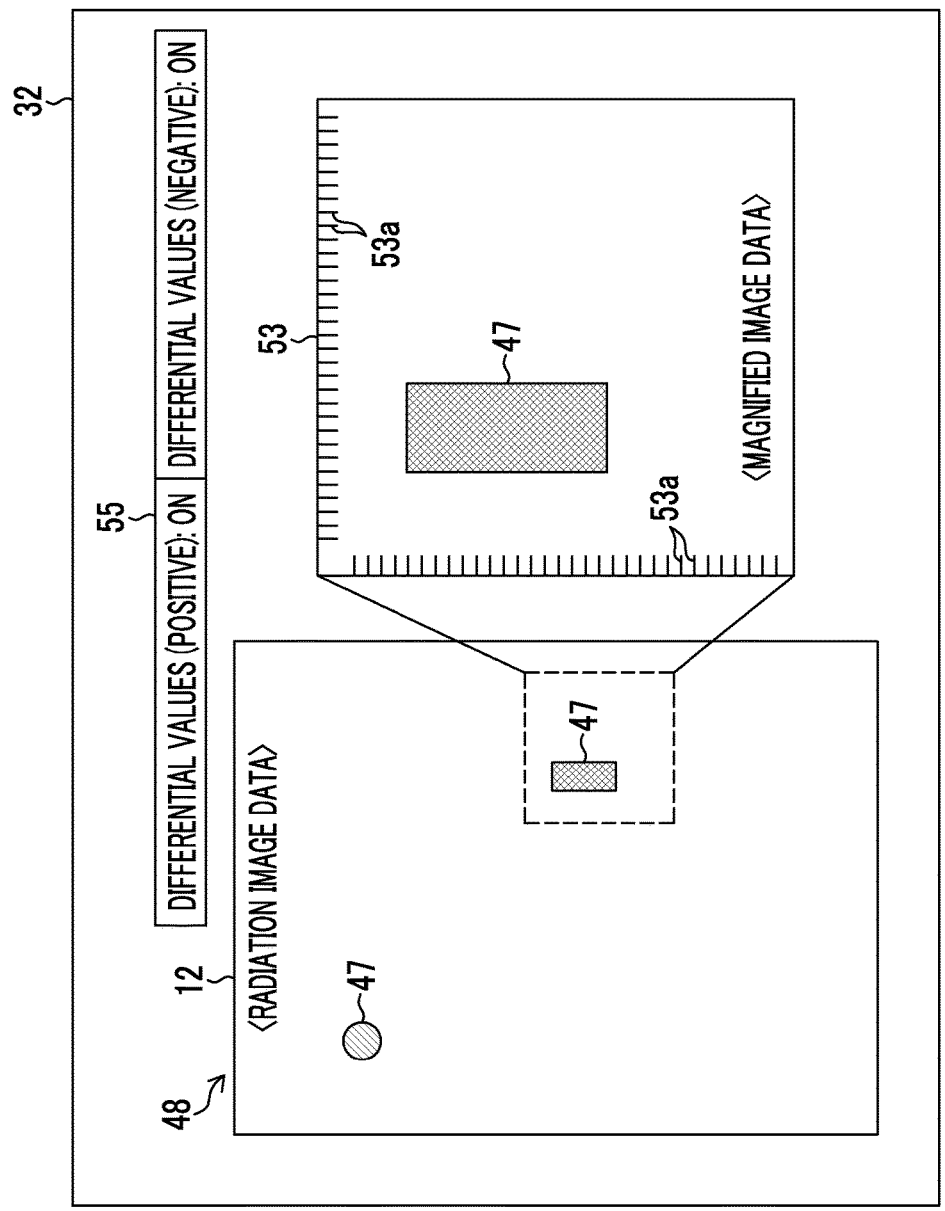

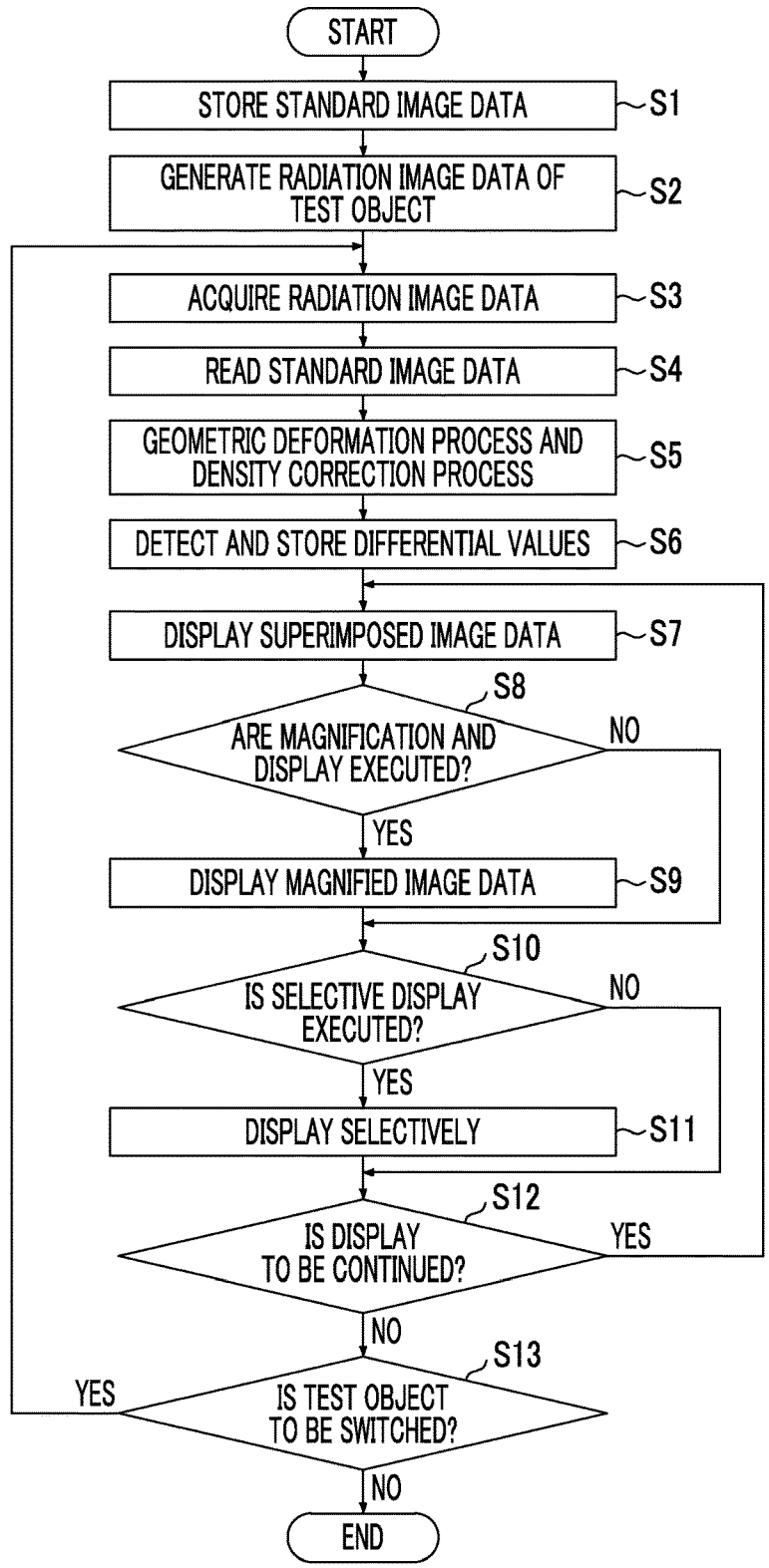

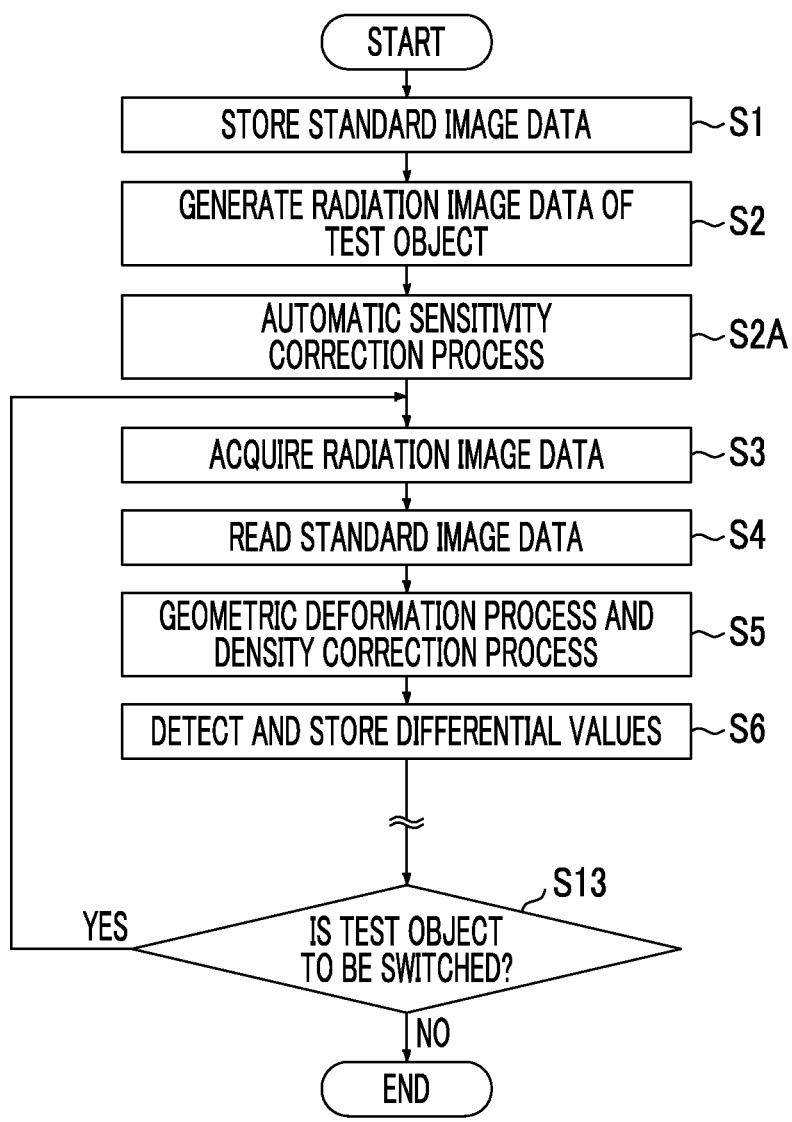

IMAGE PROCESSING DEVICE, IMAGE PROCESSING METHOD, AND PROGRAM

CROSS-REFERENCE TO RELATED APPLICATIONS

This application is a Continuation of PCT International Application No. PCT/JP2016/057052 filed on Mar. 8, 2016, which claims priority under 35 U.S.C § 119(a) to Patent Application No. 2015-093216 filed in Japan on Apr. 30, 2015, all of which are hereby expressly incorporated by reference into the present application.

BACKGROUND OF THE INVENTION

1. Field of the Invention

The present invention relates to an image processing device, an image processing method, and a non-transitory computer readable recording medium storing a program that compare a radiation image of a test object with a standard image.

2. Description of the Related Art

As a method for testing defects of various test objects such as industrial parts (products) or industrial facilities, a non-destructive testing (NDT) technique using radiation such as X-rays is known.

In such non-destructive testing technique, radiation such as X-rays is emitted to a test object, the radiation that transmitted the test object is imaged by an imaging unit, a radiation transmission image obtained by the imaging is displayed on a display unit, and an inspector observes a difference between display (digital) driving level (DDL) values of the displayed radiation transmission image to determine the presence or absence of a defect in the test object. Here, in a case in which the test object has a three-dimensionally complicated shape, it is difficult to distinguish original convex and concave of the test object from defects thereof. Further, there is a case where it is difficult to for an inspector recognize a fine difference between the DDL values due to a sensitivity difference which is a difference between ranges where respective inspectors can recognize the fine difference between the DDL values. As a result, it is difficult to directly specify a defect of a test object from a radiation transmission image.

JP2012-088291A and JP1991-137548A (JP-H03-137548A) disclose a method for determining the presence or absence of a defect of a test object on the basis of a differential image between a radiation transmission image obtained by imaging radiation that transmitted a test object and a standard image obtained by imaging radiation that transmitted a normal test object with no defect.

JP1996-146137A (JP-H08-146137A) discloses a method for obtaining a differential image between two radiation transmission images obtained by imaging radiation that transmitted a test object at different timings while relatively moving one of the test object and an imaging unit to the other, and detecting a defect image in the test object on the differential image as a double image.

JP4988482B discloses a method for detecting the presence or absence of a defect of a test object on the basis of an image obtained by offset-correcting a radiation image obtained by imaging radiation that transmitted the test object using correction image data. In JP4988482B, differential image data between a radiation image obtained by imaging radiation that transmitted an object having a uniform thickness larger than of the test object and an average image of a plurality of radiation images obtained by imaging radiation that respectively transmitted a plurality of test objects is used as the correction image data.

JP1991-209583A (JP-H03-209583A) discloses a method for removing influences other than a defect by, for example, a quadratic curve approximating process from a radiation image obtained by imaging radiation that transmitted a test object to obtain an image in which the defect is emphasized, thereby detecting the defect of the test object.

SUMMARY OF THE INVENTION

However, as defects included in a test object, there are a plurality of types of defects such as an air bubble or an impurity. In the methods disclosed in JP2012-088291A and JP1991-137548A (JP-H03-137548A), a differential region between a standard image and a radiation transmission image can be detected as a candidate of a defect in a test object, but is merely detected as the candidate of the defect without distinction even in a case in which there are different types of defects such as an air bubble or an impurity. As a result, an inspector cannot easily recognize situations (types) of defects included in the test object and distributions thereof.

In the method disclosed in JP1996-146137A (JP-H08-146137A), since radiation that transmitted a test object is imaged at different timings while one of the test object and the imaging unit is being relatively moved to the other, in a case in which a relative movement distance between the test object and the imaging unit is excessively shortened, since a difference between portions including defects in two radiation transmission images is not generated, it is not possible to detect a defect image. Further, contrarily, in a case in which the relative movement distance is excessively lengthened, due to a difference between imaging conditions (an irradiation angle in a case in which the test object is irradiated with radiation, or the like) of a test object in obtaining two radiation transmission images, it is difficult to obtain a differential image with high accuracy. Further, similar to the methods disclosed in JP2012-088291A and JP1991-137548A (JP-H03-137548A), there is a problem that it is not possible to easily recognize situations of defects included in the test object and distributions thereof.

In the method disclosed in JP4988482B, since a radiation image obtained by imaging radiation that transmitted an object having a uniform thickness larger than of a test object is necessary in generating correction image data (differential image data), it is necessary to prepare in advance the above-mentioned object different from the test object, which causes a large amount of efforts. Further, similar to the methods disclosed in JP2012-088291A and JP1991-137548A (JP-H03-137548A), there is a problem that it is not possible to easily recognize situations of defects included in the test object and distributions thereof.

In the method disclosed in JP1991-209583A (JP-H03-209583A), in removing influences other than a defect by, for example, a quadratic curve approximating process from a radiation image, a processing method for removing the influences other than the defect from the radiation image varies according to test objects or test portions. Thus, in the method disclosed in JP1991-209583A (JP-H03-209583A), it is necessary to accumulate know-how of processing methods to be applied according to test objects or test portions by making experiences of inspectors as a database, and thus, there is a case where it is not possible to easily perform detection of defects in a new test object or a new test portion.

The invention has been made in consideration of the above-mentioned problems, and an object of the invention is to provide an image processing device, an image processing method, and a non-transitory computer readable recording medium storing a program capable of rapidly and reliably recognizing situations of defects that are likely to be included in a test object and distributions thereof.

According to an aspect of the invention, there is provided an image processing device comprising: a radiation image acquisition unit that acquires a radiation image obtained by imaging a test object irradiated with radiation; a standard image storage unit that stores a standard image which is a normal radiation image of the test object imaged under the same imaging condition as in the radiation image acquired by the radiation image acquisition unit; a differential value detection unit that detects differential values of pixel values between corresponding pixels of the radiation image acquired by the radiation image acquisition unit and the standard image stored in the standard image storage unit; and a display control unit that causes a display unit to display a differential region between the radiation image and the standard image so that positive and negative of the differential values in the differential region can be determined on the basis of a detection result of the differential value detection unit.

According to the invention, it is possible to easily determine whether the differential values in the differential region displayed on the display unit are positive values or negative values.

According to another aspect of the invention, in the image processing device, the display control unit is capable of causing the display unit to selectively display any one of the differential region where the differential values are positive and the differential region where the differential values are negative. Thus, it is possible to easily recognize a distribution of the differential region where the differential values are positive and a distribution of the differential region where the differential values are negative, and thus, it is possible to easily recognize a distribution of a differential region with a possibility of a specific defect.

According to still another aspect of the invention, in the image processing device, the display control unit causes the display unit to display the differential region where absolute values of the differential values are equal to or greater than a predetermined threshold value so that the positive and negative of the differential values can be determined, on the basis of the detection result of the differential value detection unit. Thus, it is possible to cause the display unit to display only a region with a high defect possibility in the differential region so that the positive and negative of the differential values can be determined, and thus, it is possible to easily specify only a differential region with a high defect possibility. As a result, it is possible to rapidly and reliably recognize situations (types) of defects included in a test object and distributions thereof.

According to still another aspect of the invention, the image processing device further comprises a detection result storage unit that stores the detection result of the differential values detected by the differential value detection unit for each radiation image; and a threshold value change unit that changes the threshold value, and the display control unit causes, in a case in which the threshold value is changed by the threshold value change unit, the display unit to display the differential region where the absolute values of the differential values are equal to or greater than the threshold value after the change so that the positive and negative of the differential values can be determined, on the basis of the detection result of the differential values stored in the detection result storage unit, for each radiation image. Thus, on the basis of the detection result of the previous differential values stored in the detection result storage unit, it is possible to cause the display unit to redisplay the differential region corresponding to the threshold value after change with respect to the previous radiation image. As a result, even in a case in which the threshold value is changed, it is possible to easily recognize a differential region with a high defect possibility using the threshold value after change as a standard.

According to still another aspect of the invention, the image processing device further comprises a radiation image storage unit that stores the radiation image; and a storage control unit that stores the detection result of the differential values detected by the differential value detection unit in the radiation image storage unit in association with the radiation image. Thus, even in a case in which a threshold value for determining a defect possibility of a differential region in a test object is changed, it is possible to determine the defect possibility of the differential region using a new threshold value as a reference, on the basis of the detection result of the previous differential values stored in the radiation image storage unit. As a result, it is possible to specify a test object having a defect possibility according to a new standard.

According to still another aspect of the invention, the image processing device further comprises a first image correction unit that performs, with respect to the standard image stored in the standard image storage unit, a process of correcting a density difference between the standard image and the radiation image before detection of the differential values in the differential value detection unit. Thus, it is possible to reduce a density difference that does not result from a defect of a test object that is a test target.

According to still another aspect of the invention, the image processing device further comprises a second image correction unit that performs, with respect to the standard image stored in the standard image storage unit, a process of matching an inclination and a shape of the standard image with an inclination and a shape of the radiation image before detection of the differential values in the differential value detection unit. Thus, it is possible to prevent errors of an inclination and a shape that do not result from a defect of a test object that is a test target from occurring between the standard image data and the radiation image data.

According to still another aspect of the invention, the image processing device further comprises a third image correction unit that performs, with respect to a plurality of the radiation images acquired by the radiation image acquisition unit, a process of correcting a density difference due to variation in the imaging condition for each radiation image, and the differential value detection unit detects differential values of pixel values between corresponding pixels of the radiation image corrected by the third image correction unit and the standard image for each radiation image. Thus, it is possible to correct a density difference of radiation images due to variation in imaging conditions.

According to still another aspect of the invention, in the image processing device, the display control unit causes the display unit to display a superimposed image obtained by superimposing the differential region on the radiation image. Thus, it is possible to easily recognize a position where a differential region in a test object is generated.

According to still another aspect of the invention, in the image processing device, the display control unit causes the display unit to display a magnified image obtained by magnifying the differential region in the superimposed image together with the superimposed image. Thus, it is possible to recognize a detailed state of a differential region, and thus, it is possible to easily determine whether the differential region is a defect.

According to still another aspect of the invention, in the image processing device, the display control unit gives different colors to the differential region where the differential values are positive and the differential region where the differential values are negative, respectively, and causes the display unit to display the result. Thus, it is possible to easily determine positive and negative of differential values in a differential region.

According to still another aspect of the invention, there is provided an image processing method comprising: a radiation image acquisition step of acquiring a radiation image obtained by imaging a test object irradiated with radiation; a standard image storage step of storing a standard image which is a normal radiation image of the test object imaged under the same imaging condition as in the radiation image acquired in the radiation image acquisition step, in a standard image storage unit; a differential value detection step of detecting differential values of pixel values between corresponding pixels of the radiation image acquired in the radiation image acquisition step and the standard image stored in the standard image storage unit; and a display control step of causing a display unit to display a differential region between the radiation image and the standard image so that positive and negative of the differential values in the differential region can be determined on the basis of a detection result in the differential value detection step.

According to still another aspect of the invention, there is provided a non-transitory computer readable recording medium storing a program that causes a computer of an image processing device to function as: a radiation image acquisition unit that acquires, using an imaging unit that images a test object irradiated with radiation, a radiation image of the test object; a differential value detection unit that detects differential values of pixel values between corresponding pixels of the radiation image acquired by the radiation image acquisition unit and a standard image which is a normal radiation image of the test object imaged under the same imaging condition as in the radiation image acquired by the radiation image acquisition unit; and a display control unit that causes a display unit to display a differential region between the radiation image and the standard image so that positive and negative of the differential values in the differential region can be determined on the basis of a detection result of the differential value detection unit.

According to the image processing device, the image processing method, and the non-transitory computer readable recording medium storing the program of the invention, it is possible to rapidly and reliably recognize situations of defects that are likely to be included in a test object and distributions thereof.

BRIEF DESCRIPTION OF THE DRAWINGS

FIG. 3 is diagrams illustrating a density correction process in a standard image correction unit, and are histograms illustrating distributions of pixel values of pixels that form standard image data and radiation image data, respectively.

FIG. 6 is a front view of an image displayed on a display surface of a display unit by a display control unit.

FIG. 8 is a flowchart illustrating a flow of a display process of a differential region in the non-destructive testing apparatus according to the first embodiment.

FIG. 16 is a flowchart illustrating a flow of a display process of a differential region in the non-destructive testing apparatus according to the third embodiment, particularly, a flow of an automatic sensitivity correction process.

DESCRIPTION OF THE PREFERRED EMBODIMENTS

[Overall Configuration of Non-Destructive Testing Apparatus According to First Embodiment]

Figure 1:
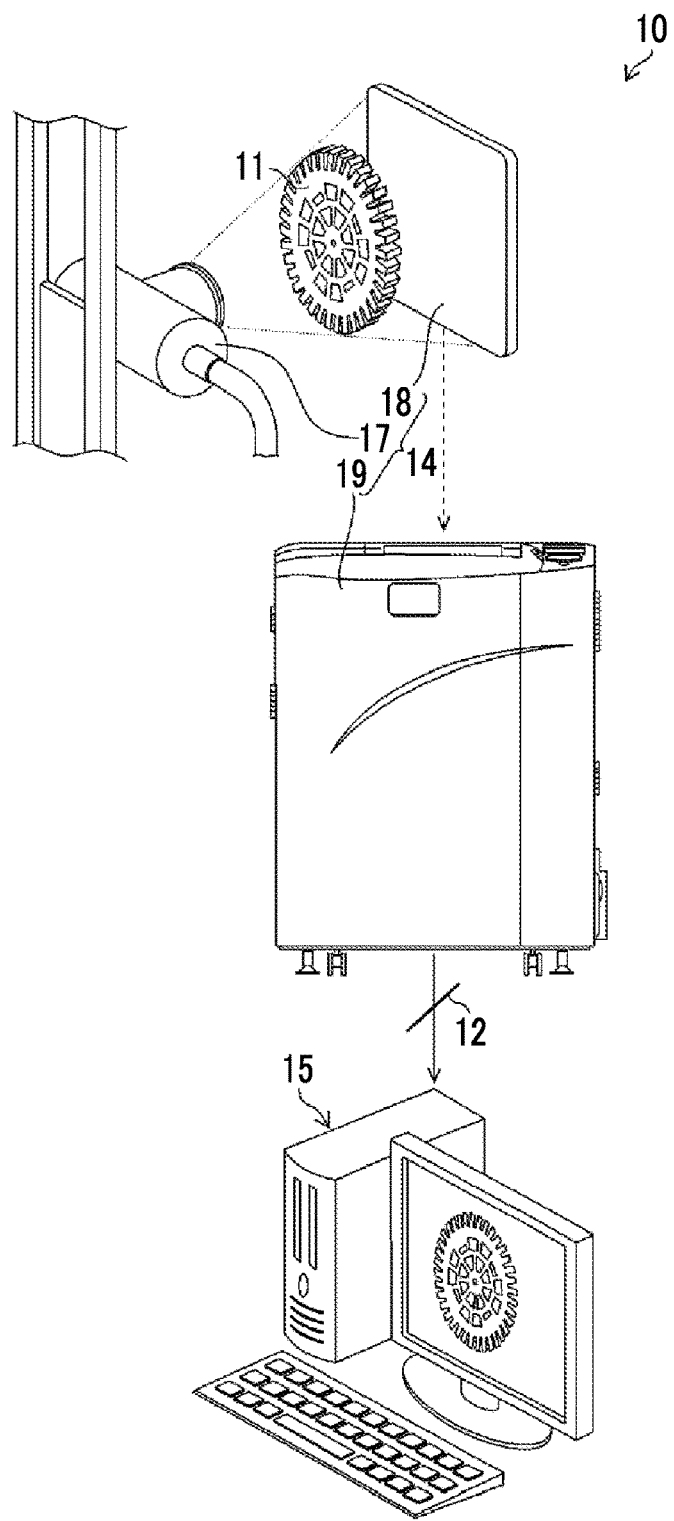
FIG. 1 is a schematic diagram illustrating an overall configuration of a non-destructive testing apparatus according to a first embodiment.

FIG. 1 is a schematic diagram illustrating an overall configuration of a non-destructive testing apparatus 10 that performs a non-destructive test of a test object 11 such as an industrial part or an industrial facility. As shown in FIG. 1, the non-destructive testing apparatus 10 acquires radiation image data 12 (corresponding to a radiation image in the invention) of the test object 11. Further, the non-destructive testing apparatus 10 displays a region having a defect possibility in the test object 11 on the basis of the radiation image data 12. Here, the defect means bubbles, impurities, scars, or the like included in the test object 11, and has a size or a length that exceeds a predetermined standard, but a standard for determining the defect is not particularly limited.

The non-destructive testing apparatus 10 generally includes an imaging unit 14 that generates the radiation image data 12 of a test object, and an image processing device 15 that is configured by an arithmetic processing device such as a personal computer.

The imaging unit 14 includes a radiation source 17, an imaging plate 18, and an imaging plate reader 19.

The radiation source 17 irradiates the test object 11 with radiation (for example, X-rays). A distance between the radiation source 17 and the test object 11, and an irradiation angle in a case in which the radiation source 17 irradiates the test object 11 with radiation may be adjusted to desired values, respectively.

The imaging plate 18 is disposed at a position that faces the radiation source 17 with the test object 11 being interposed therebetween, and is disposed at a position close to the test object 11. Radiation that transmitted the test object 11 is incident onto the imaging plate 18 by irradiation of radiation from the radiation source 17 to the test object 11, and energy information based on the dose of the incident radiation is accumulated thereon as radiation image information. The imaging plate 18 on which the radiation image information is accumulated is set in the imaging plate reader 19.

In this embodiment, a plate type plate is used as the imaging plate 18, but its shape is not particularly limited. For example, a curved type plate may be used. Further, an X-ray film or the like may be used instead of the imaging plate 18.

The imaging plate reader 19 reads the radiation image information accumulated on the imaging plate 18, and generates the radiation image data 12 of the test object 11 on the basis of the radiation image information. Thus, the radiation image data 12 of the test object 11 is obtained by imaging the radiation that transmitted the test object 11. The radiation image data 12 is generated by a digital imaging and communication in medicine (DICOM) file format in this embodiment, but its format is not particularly limited. Further, the image processing device 15 is connected to the imaging plate reader 19 through a wired or wireless communication network, so that the generated radiation image data 12 is output to the image processing device 15.

The image processing device 15 detects differential values of pixel values between corresponding pixels of the radiation image data 12 of the test object 11 input from the imaging plate reader 19 and standard image data 20 which is radiation image data of a normal test object 11 (corresponding to a standard image in the invention, see FIG. 2), and discriminately displays a differential region between the radiation image data 12 and the standard image data 20 on the basis of the detection result.

<Configuration of Image Processing Device>

Figure 2:
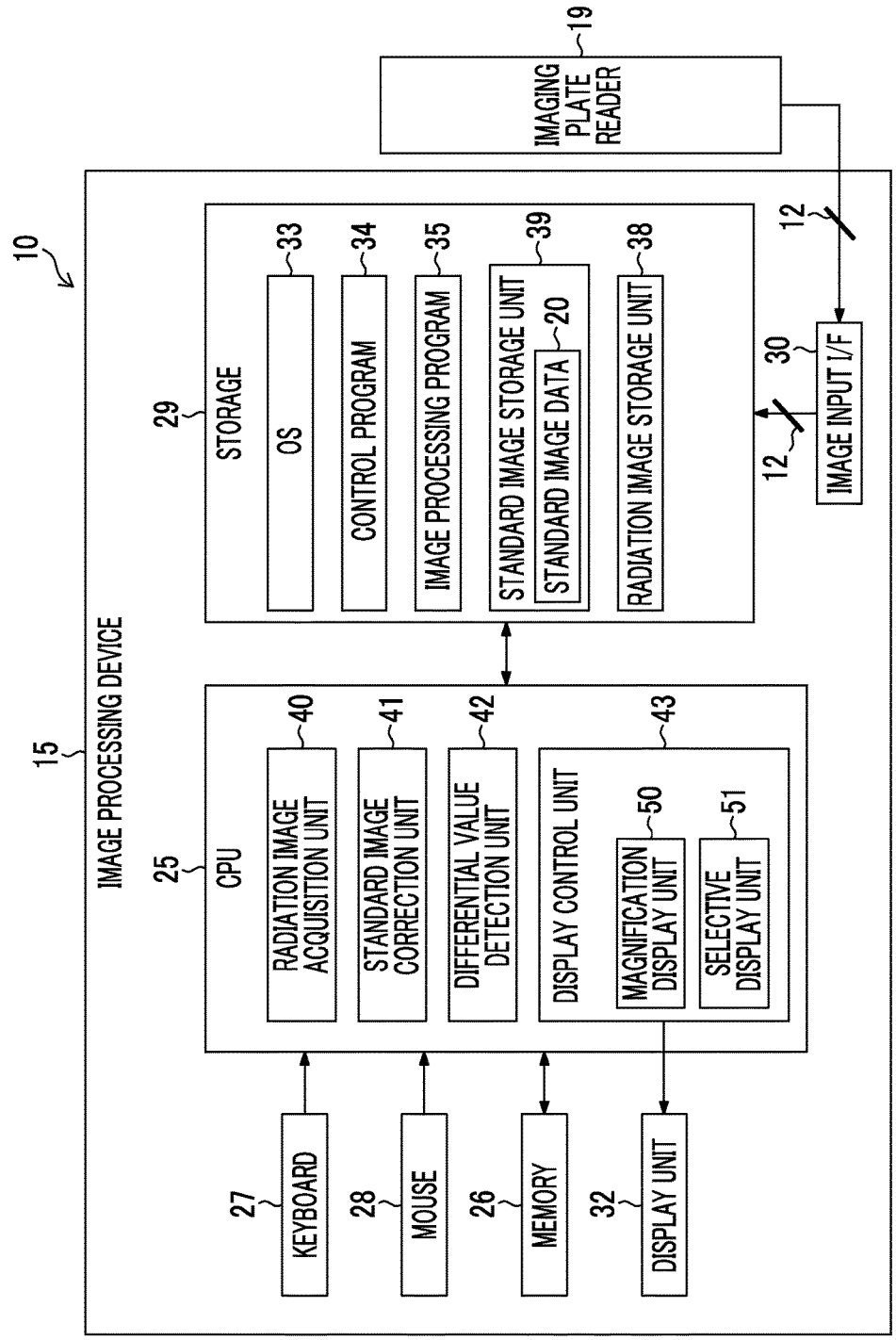
FIG. 2 is a block diagram illustrating an electric configuration of an image processing device according to the first embodiment.

FIG. 2 is a block diagram illustrating an electric configuration of the image processing device 15. As shown in FIG. 2, the image processing device 15 includes a central processing unit (CPU) 25, a memory 26, a keyboard 27, a mouse 28, a storage 29, an image input/output interface (I/F) 30, and a display unit 32.

The CPU 25 loads a program stored in the storage 29 to the memory 26, and executes processes according to the program to generally control respective units of the image processing device 15. The memory 26 is a work memory used in a case in which the CPU 25 executes the processes. Further, a variety of data generated by the CPU 25 is temporarily stored in the memory 26. The keyboard 27 and the mouse 28 are known peripheral input devices used in an operation of the image processing device 15.

As the storage 29, a hard disk drive, a non-volatile memory, or the like is used. The storage 29 stores various programs such as an operating system (hereinafter, referred to as an "OS") 33, a control program 34, or an image processing program 35.

The OS 33 is basic software that manages the image processing device 15. The control program 34 is a control program of each unit of the image processing device 15. The CPU 25 generally controls respective units of the image processing device 15 according to the control program 34. The image processing program 35 corresponds to a program of the invention, and is a program for displaying the differential region between the radiation image data 12 and the standard image data 20.

Further, the storage 29 is provided with a radiation image storage unit 38 that stores the radiation image data 12 that is input to the image processing device 15 from the imaging plate reader 19, and a standard image storage unit 39 that stores the standard image data 20.

The standard image data 20 is radiation image data of a normal test object 11 that is determined to have no defect that is determined to be defective and to be normal in advance by an inspector, and is obtained by imaging under the same imaging conditions as those of the radiation image data 12 of the test object 11 that is a test target. The imaging conditions include a distance between the radiation source 17 and the test object 11, an intensity and an incident angle of radiation emitted to the test object 11 from the radiation source 17, a geometrical position of the test object 11 indicating a relative position or a posture of the test object 11 with respect to the radiation source 17 or the imaging plate 18, the kind or the shape of the imaging plate 18, and the like. Accordingly, the same imaging conditions refer to imaging conditions in which the test object 11 that is the test target and the normal test object 11 are the same, and differential values of pixel values between the corresponding pixels of the radiation image data 12 and the standard image data 20 (differential values of pixel values between the corresponding pixels due to a defect included in the test object 11 that is a test target) can be detected.

The standard image data 20 is individually stored in the standard image storage unit 39 according to the kind of the test object 11 and imaging conditions.

The image input I/F 30 is connected to the imaging plate reader 19 through various communication networks as described above. The image input I/F 30 acquires the radiation image data 12 from the imaging plate reader 19, and sequentially stores the acquired radiation image data 12 in the radiation image storage unit 38.

As the display unit 32, various known display devices such as a liquid crystal display are used, for example. The display unit 32 displays the differential region between the radiation image data 12 and the standard image data 20 under the control of the CPU 25. As the display unit 32, a display with a touch panel by which a user can operate an image processing device may be used instead of the keyboard 27 and the mouse 28.

In a case in which the image processing program 35 is operated, the CPU 25 executes processes according to the image processing program 35, thereby functioning as a radiation image acquisition unit 40, a standard image correction unit 41, a differential value detection unit 42, and a display control unit 43.

The radiation image acquisition unit 40 functions as a radiation image acquisition unit in the invention with the above-described image input I/F 30. The radiation image acquisition unit 40 acquires the radiation image data 12 specified by the keyboard 27, the mouse 28 or the like from the radiation image storage unit 38, and outputs the radiation image data 12 to the standard image correction unit 41, the differential value detection unit 42, and the display control unit 43, respectively.

[Image Correction Process]

The standard image correction unit 41 functions as a first image correction unit and a second image correction unit of the invention. The standard image correction unit 41 performs an image correction process with respect to the standard image data 20 before detection of differential values of pixel values between the corresponding pixels of the radiation image data 12 and the standard image data 20 in the differential value detection unit 42 (which will be described later).

The standard image data 20 and the radiation image data 12 are obtained by imaging under the same imaging conditions, but there is a case where variation occurs in the imaging conditions due to errors of the intensity and an incident angle of radiation emitted to the test object 11, an error of a geometric position of the test object 11, or the like. As a result, there is a case where an error of an inclination and a shape that is not based on a defect of the test object 11 that is the test target and a density difference (difference between pixel values of pixels) occur between the standard image data 20 and the radiation image data 12.

The standard image correction unit 41 reads the standard image data 20 corresponding to the radiation image data 12 acquired by the radiation image acquisition unit 40 from the standard image storage unit 39. Further, the standard image correction unit 41 performs a geometric deformation process of matching an inclination and the shape of the standard image data 20 with an inclination and the shape of the radiation image data 12, and a density correction process of correcting a density difference with the radiation image data 12, with respect to the read standard image data 20. That is, the standard image correction unit 41 functions as the second image correction unit of the invention in a case in which the geometric deformation process is performed, and functions as the first image correction unit of the invention in a case in which the density correction process is performed.

<Geometric Deformation Process>

The standard image correction unit 41 detects, in a case in which the geometric deformation process is performed, a plurality of corresponding points of which features match (or approximately match) each other between the standard image data 20 and the radiation image data 12. A method for detecting the corresponding points is not particularly limited, and for example, a known technique such as a block matching method may be used.

Then, the standard image correction unit 41 estimates geometric deformation parameters for geometrically deforming the standard image data 20 so that coordinates of respective corresponding points of the standard image data 20 match (or approximately match) coordinates of respective corresponding points of the radiation image data 12. Further, the standard image correction unit 41 performs the geometric deformation process with respect to the standard image data 20 on the basis of the estimated geometric deformation parameters. As such a geometric deformation processing method, a known technique such as projective transformation that uses projective transformation parameters, affine transformation that uses affine transformation parameters, or Helmert transformation that uses Helmert transformation parameters may be used.

<Density Correction Process>

FIGS. 3A and 3B illustrate a density correction process in the standard image correction unit 41, and are histograms showing distributions of pixel values of pixels that form the standard image data 20 and the radiation image data 12, respectively. In FIGS. 3A and 3B, a lateral axis represents a pixel number indicating a pixel that forms the standard image data 20 and the radiation image data 12, respectively, and a longitudinal axis represents a pixel value of each pixel of the standard image data 20 and the radiation image data 12. For example, in a case in which the standard image data 20 and the radiation image data 12 are formed by m×n (m and n are arbitrary natural numbers) pixels, the pixel number is 1 to m×n. Further, in a case in which the standard image data 20 and the radiation image data 12 correspond to 8-bit image data, respectively, the pixel value is 0 to 255.

As shown in (a) of FIG. 3, the standard image correction unit 41 detects, in a case in which the density correction process is performed, a pixel value (displayed by a solid line in the figure) of each pixel of the standard image data 20 and a pixel value (displayed by a dashed line in the figure) of each pixel of the radiation image data 12, respectively. Here, in a case in which a defect is included in the test object 11, a pixel value of a pixel included in a defect region F corresponding to the defect in the radiation image data 12 greatly changes compared with pixel values of pixels included in a region other than the defect region F.

Then, the standard image correction unit 41 analyzes a distribution of pixel values of respective pixels of the radiation image data 12, detects a region where the amount of change of pixel values is larger than a predetermined value as the defect region F, and detects a region other than the defect region F as a normal region. Further, the standard image correction unit 41 detects a corresponding region in the standard image data 20 corresponding to the normal region in the radiation image data 12. Then, the standard image correction unit 41 calculates a correction value for correcting a pixel value of each pixel of the standard image data 20 so that a pixel value of each pixel in the corresponding region of the standard image data 20 matches a pixel value of each pixel in the normal region of the radiation image data 12. Further, the standard image correction unit 41 corrects the pixel value of each pixel of the standard image data 20 on the basis of the calculated correction value.

As shown in (b) of FIG. 3, by correcting the pixel value of the standard image data 20, it is possible to correct a difference between the pixel value of each pixel in the normal region of the radiation image data 12 and the pixel value of each pixel in the corresponding region of the standard image data 20, that is, a density difference between the normal region of the radiation image data 12 and the corresponding region of the standard image data 20. As a result, in the differential value detection unit 42 (which will be described later), in a case in which differential values of pixel values between the corresponding pixels of the radiation image data 12 and the standard image data 20 are detected, differential values of pixel values between the corresponding pixels in the normal region can be set to be almost zero.

The standard image correction unit 41 outputs the standard image data 20 after the image correction process, subjected to the geometric deformation process and the density correction process, to the differential value detection unit 42.

[Differential Value Detection Process]

Figure 4:
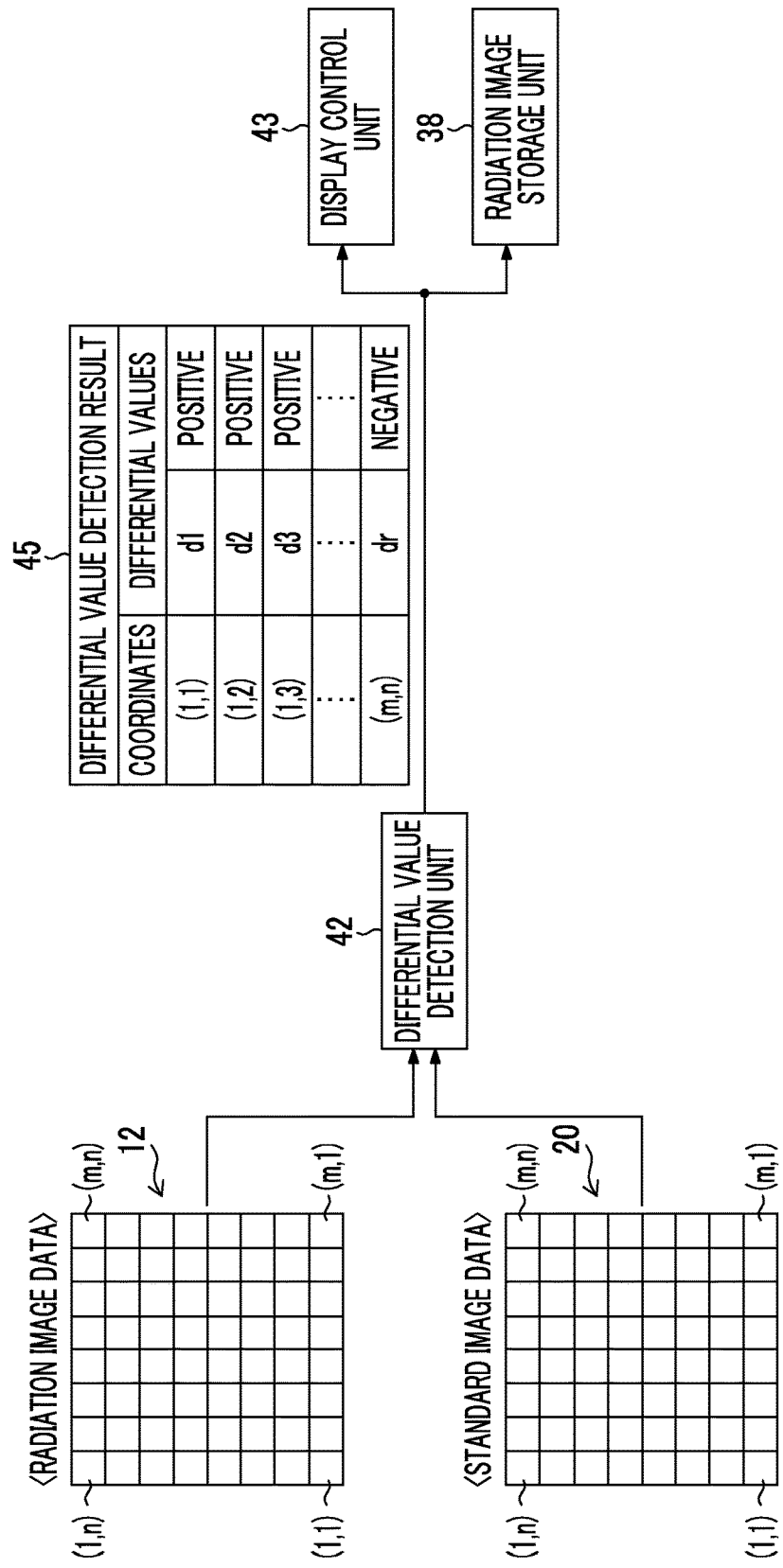
FIG. 4 is a diagram illustrating a detection process of differential values of pixel values between corresponding pixels of radiation image data and standard image data in a differential value detection unit.

FIG. 4 is a diagram illustrating a detection process of differential values of pixel values between the corresponding pixels of the radiation image data 12 and the standard image data 20 in the differential value detection unit 42. As shown in FIG. 4, the differential value detection unit 42 detects differential values of pixel values between the corresponding pixels of the radiation image data 12 input from the radiation image acquisition unit 40 and the standard image data 20 input from the standard image correction unit 41, for each pixel. Here, the differential value in this embodiment is a value obtained by subtracting "a pixel value of a pixel of the standard image data 20" from "a pixel value of a pixel of the radiation image data 12", and becomes any one of a positive value, a negative value, and zero (including almost zero).

For example, a detection process of a differential value in a case in which the radiation image data 12 and the standard image data 20 are configured by m×n pixels, coordinates of pixels in the lower left corners in the figures in the radiation image data 12 and the standard image data 20 are set to (1, 1), and coordinates of pixels in the upper right corners in the figures are set to (m, n) will be described.

First, the differential value detection unit 42 calculates a differential value between a pixel value of a pixel of coordinates (1, 1) of the radiation image data 12 and a pixel value of a pixel of coordinates (1, 1) of the standard image data 20. Then, the differential value detection unit 42 calculates a differential value between a pixel value of a pixel of coordinates (1, 2) of the radiation image data 12 and a pixel value of a pixel of coordinates (1, 2) of the standard image data 20. Thereafter, similarly, the differential value detection unit 42 calculates differential values between pixel values of all the remaining pixels of the radiation image data 12 and pixel values of respective pixels of the standard image data 20. In this way, the differential values of the pixel values between the corresponding pixels (hereinafter, between pixels on the same coordinates) of the radiation image data 12 and the standard image data 20 are detected by the differential value detection unit 42, and a differential value detection result 45 indicating detection results of the differential values is obtained.

In the differential value detection result 45, absolute values (d1, d2, . . . , dr) of differential values of pixel values of respective pixels of the radiation image data 12 and the standard image data 20, and information indicating positive and negative thereof are registered, with respect to every coordinates of the respective pixels of the radiation image data 12, for example. With respect to a pixel for which the differential value is zero, and a pixel for which the absolute value of the differential value becomes smaller than a predetermined lower limit value and becomes substantially zero, the registration (storage) of the differential value in the differential value detection result 45 may not be performed. Thus, it is possible to reduce the amount of data of the differential value detection result 45. Further, in this embodiment, the absolute values (d1, d2, . . . , dr) of the differential values and the information indicating the positive and negative are registered in the differential value detection result 45, but the differential values (+d1, +d2, . . . , −dr) from which the positive and negative can be determined may be registered as they are.

Further, the differential value detection unit 42 respectively stores the differential value detection result 45 in the radiation image storage unit 38 and the display control unit 43. That is, the differential value detection unit 42 also functions as a storage control unit in the invention.

Figure 5:
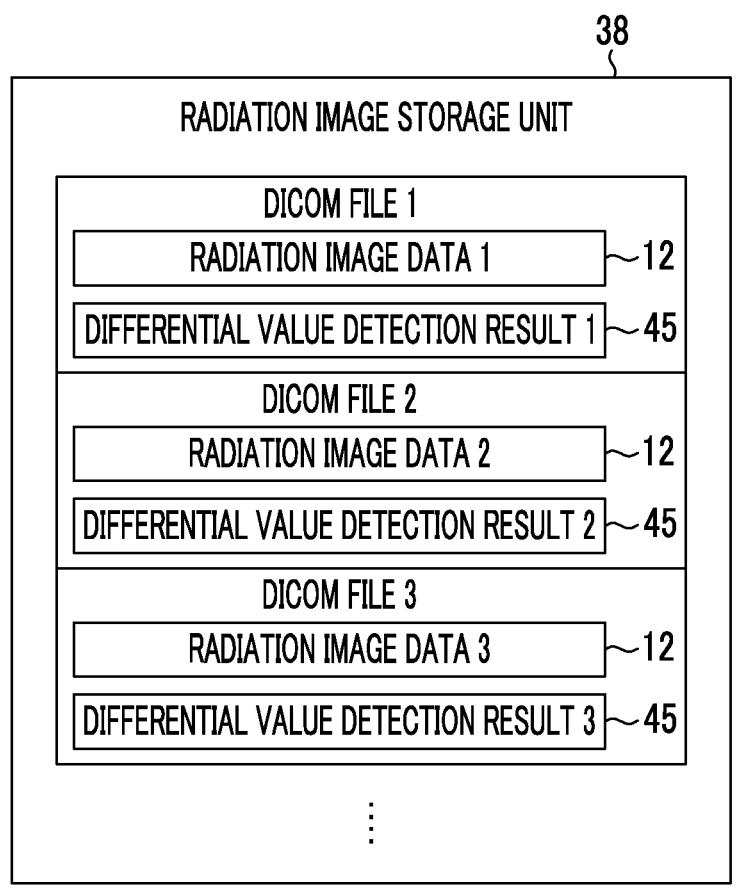
FIG. 5 is a diagram illustrating a storage format of a differential value detection result in a radiation image storage unit.

FIG. 5 is a diagram illustrating a storage format of the differential value detection result 45 in the radiation image storage unit 38. As shown in FIG. 5, the above-described radiation image data 12 is stored in the radiation image storage unit 38 in a DICOM file format. The differential value detection result 45 input to the radiation image storage unit 38 from the differential value detection unit 42 is stored as additional information in a DICOM file of the corresponding radiation image data 12. Thus, in the radiation image storage unit 38, the differential value detection result 45 is stored in association with the corresponding radiation image data 12. In other words, the differential value detection result 45 is stored for each piece of radiation image data 12. That is, the radiation image storage unit 38 also functions as a detection result storage unit in the invention.

[Display Control of Differential Region]

Returning to FIG. 2, the display control unit 43 causes the display unit 32 to display a differential region 47 (see FIG. 6) between the radiation image data 12 and the standard image data 20 on the basis of the differential value detection result 45 input from the differential value detection unit 42 so that positive and negative of the differential values in the differential region 47 can be determined. Further, the display control unit 43 functions as a magnification display unit 50 that performs magnification and display of the differential region 47, and a selective display unit 51 that causes the display unit 32 to selectively display the differential region 47 according to the positive and negative of the differential values.

FIG. 6 is a front view of an image displayed on a display surface of the display unit 32 by the display control unit 43. As shown in FIG. 6, the display control unit 43 determines a region formed by pixels where differential values are generated as the differential region 47 of the radiation image data 12 and the standard image data 20 on the basis of the differential value detection result 45 input from the differential value detection unit 42. That is, the display control unit 43 determines a region formed by pixels included in the above-described defect region F shown in FIGS. 3A and 3B as the differential region 47. Differential values of pixel values between the corresponding pixels in a normal region other than the defect region F become approximately zero by the above-described density correction process in the standard image correction unit 41. Thus, in a case in which absolute values of the differential values are smaller than a predetermined lower limit value, the display control unit 43 determines that the differential values are substantially zero. Thus, the display control unit 43 does not determine the normal region as the differential region 47.

Then, the display control unit 43 generates a superimposed image data 48 obtained by superimposing the differential region 47 on the radiation image data 12 input from the radiation image acquisition unit 40, and causes the display unit 32 to display the superimposed image data 48.

Here, the display control unit 43 causes the display unit 32 to display the differential region 47 in the superimposed image data 48 so that positive and negative of the differential values in the differential region 47 can be determined. Specifically, the display control unit 43 gives different colors to the differential region 47 (displayed by hatching in the figure) where the differential values are positive (plus) and the differential region 47 (displayed by shading in the figure) where the differential values are negative (minus), and causes the display unit 32 to display the result. For example, in a case in which the radiation image data 12 in the superimposed image data 48 is monochromatically displayed, the differential region 47 where the differential values are positive is displayed by a red color, and the differential region 47 where the differential values are negative is displayed by a blue color. Here, the kinds of colors given to the differential region 47 are not particularly limited.

In a case in which the differential region 47 is color-displayed, the display density may be changed according to the size of the absolute values of the differential values. For example, as the absolute values of the differential values increase, the display density may gradually increase. Since as the absolute values of the differential values increase, a possibility that the differential region 47 may be a defect increases, an inspector can easily specify the differential region 47 with a high defect possibility. Further, in a case in which the differential region 47 is displayed, the differential values may be displayed at the same time, or a variety of displays through which an inspector can determine the magnitudes of the absolute values of the differential values in the differential region 47 may be determined. Thus, even in a case in which a plurality of types of defects having positive differential values or a plurality of types of defects having negative differential values are present, in a case in which the sizes of the differential values are different from each other according to the types of the defects, it is possible to specify the types of the defects.

The differential region 47 that is color-displayed on the display unit 32 is a region with a possibility that there is a defect in the test object 11. Further, the differential region 47 where the differential values are positive is a region with a possibility that a defect such as an air bubble (referred to as a "pore") is included in the test object 11, and the differential region 47 where the differential values are negative is a region with a possibility that a defect such as impurities is included in the test object 11.

The magnification display unit 50 generates magnified image data 53 (referred to as loupe screen data) obtained by magnifying a frame region (indicated by a rectangular dot line frame in the figure) including the differential region 47 in the superimposed image data 48, and causes the display unit 32 to display the magnified image data 53 together with the above-described superimposed image data 48. A scale 53a indicating an actual size of the differential region 47 is displayed on the magnified image data 53. Thus, an inspector can rapidly and accurately specify the actual size of the differential region 47, and thus, it is possible to determine whether the differential region 47 is a defect. Since the above-described frame region can be moved by the keyboard 27, the mouse 28, or the like, the inspector can freely select the differential region 47 to be magnified and displayed as the magnified image data 53.

Further, turning on and off of the display of the magnified image data 53 may be switched by the keyboard 27, the mouse 28, or the like. Although not shown, in a case in which the display of the magnified image data 53 is turned off, the display control unit 43 causes the display unit 32 to individually display the superimposed image data 48.

The selective display unit 51 can selectively display at least one of the differential region 47 where the differential values are positive and the differential region 47 where the differential values are negative on the display unit 32, on the basis of a display instruction input through the keyboard 27, the mouse 28, or the like. Further, the selective display unit 51 causes the display unit 32 to display an information display section 55 for indicating whether the display of each of the differential region 47 where the differential values are positive and the differential region 47 where the differential values are negative is turned on or off.

Figure 7A:
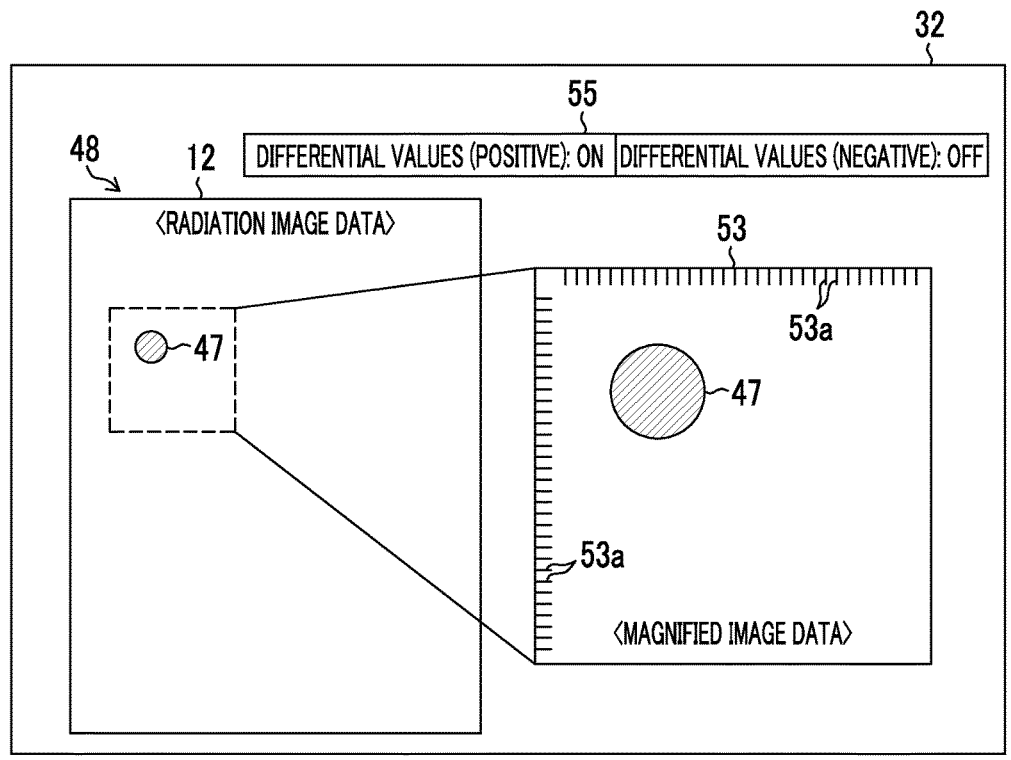
FIGS. 7A and 7B are diagrams illustrating selective displays of a differential region where differential values become positive and a differential region where differential values become negative.
Figure 7B:
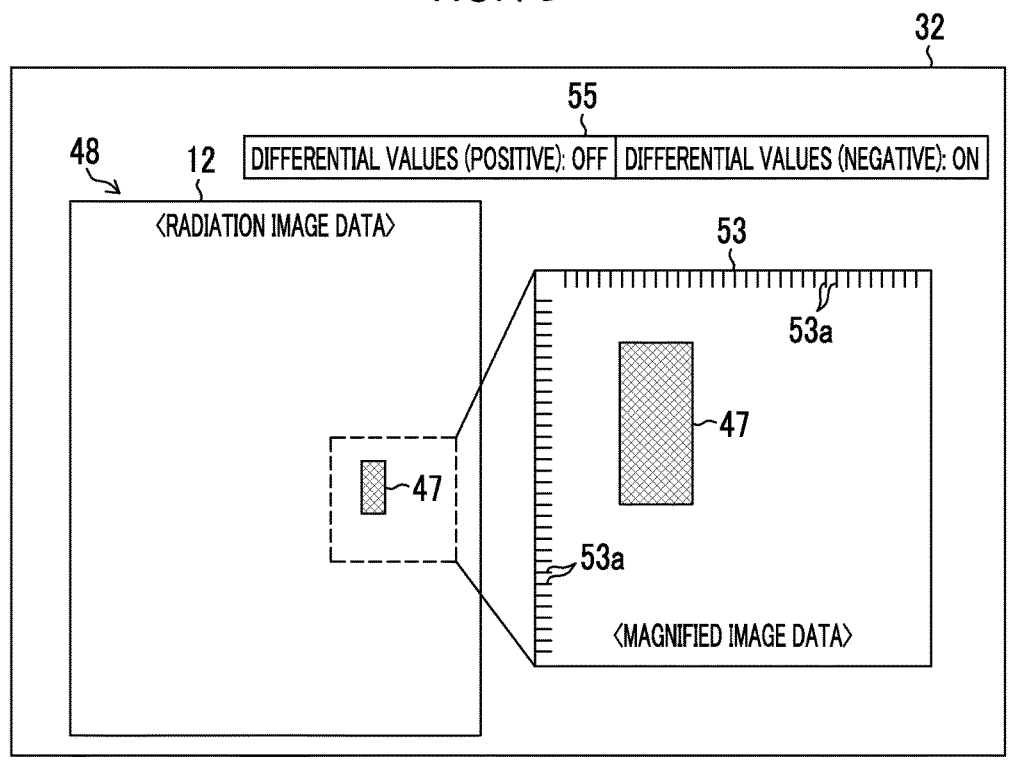

FIGS. 7A and 7B are diagrams illustrating selective displays of the differential region 47 where the differential values are positive and the differential region 47 where the differential values are negative. As shown in FIG. 7A, in a case in which a display instruction for only the differential region 47 where the differential values are positive is given through the keyboard 27, the mouse 28, or the like, the selective display unit 51 displays only the differential region 47 where the differential values are positive on the display unit 32 on the basis of the differential value detection result 45, and displays information indicating the result in the information display section 55.

As shown in FIG. 7B, in a case in which a display instruction for only the differential region 47 where the differential values are negative is given through the keyboard 27, the mouse 28, or the like, the selective display unit 51 displays only the differential region 47 where the differential values are negative on the display unit 32 on the basis of the differential value detection result 45, and displays information indicating the result in the information display section 55.

In a case in which an inspector directly observes the radiation image data 12, the inspector can turn off the display of each of the differential region 47 where the differential values are positive and the differential region 47 where the differential values are negative. Thus, the inspector directly observes a portion corresponding to the differential region 47 of the radiation image data 12, thereby determining whether the differential region 47 is a defect.

[Operation of Non-destructive Testing Apparatus According to First Embodiment]

Next, an operation (corresponding to an image processing method in the invention) of the non-destructive testing apparatus 10 having the above-described configuration will be described with reference to FIG. 8. FIG. 8 is flowchart illustrating a flow of a display process of the differential region 47 in the non-destructive testing apparatus 10.

As shown in FIG. 8, an inspector performs imaging of a normal test object 11 under the same imaging conditions as in the test object 11 which is a test target using the non-destructive testing apparatus 10 in advance to generate the standard image data 20, and stores the standard image data 20 in the standard image storage unit 39 (step S1, corresponding to a standard image storage step in the invention). In a case in which a plurality of types of test objects 11 that are test targets are present, or in a case in which a plurality of types of imaging conditions are present, the standard image data 20 is generated according to the types of the test objects 11 and the imaging conditions, and is stored in the standard image storage unit 39.

The inspector disposes the test object 11 that is a test target between the radiation source 17 and the imaging plate 18. Then, in a case in which the inspector performs a test starting operation, radiation is emitted from the radiation source 17 toward the test object 11. The radiation transmitted the test object 11 to then be incident onto the imaging plate 18. Thus, energy information based on the dose of the incident radiation is accumulated on the imaging plate 18 as radiation image information. The imaging plate 18 is set in the imaging plate reader 19.

The imaging plate reader 19 receives a reading starting operation from the inspector, and reads the radiation image information accumulated on the imaging plate 18. Further, the imaging plate reader 19 generates the radiation image data 12 of the test object 11 in a DICOM file format on the basis of the read radiation image information, and outputs the result to the image processing device 15 (step S2). The image input I/F 30 of the image processing device 15 acquires the radiation image data 12 from the imaging plate reader 19, and stores the radiation image data 12 in the radiation image storage unit 38. Thereafter, similarly, the radiation image data 12 with respect to all the test objects 11 that are test targets is acquired and is stored in the radiation image storage unit 38.

Then, the inspector operates the image processing program 35 in the image processing device 15. Thus, the CPU 25 of the image processing device 15 functions as the radiation image acquisition unit 40, the standard image correction unit 41, the differential value detection unit 42, and the display control unit 43.

In a case in which the inspector specifies the radiation image data 12 for performing a test using the keyboard 27, the mouse 28, or the like, the radiation image acquisition unit 40 acquires the specified radiation image data 12 from the radiation image storage unit 38 (step S3, corresponding to a radiation image acquisition step in the invention). Further, the radiation image acquisition unit 40 outputs the acquired radiation image data 12 to the standard image correction unit 41, the differential value detection unit 42, and the display control unit 43, respectively.

Then, the standard image correction unit 41 reads the standard image data 20 corresponding to the radiation image data 12 input from the radiation image acquisition unit 40 from the standard image storage unit 39 (step S4). Further, the standard image correction unit 41 performs the above-described geometric deformation process and density correction process with respect to the read standard image data 20, and outputs the standard image data 20 after the respective processes to the differential value detection unit 42 (step S5).

Through the geometric deformation process, it is possible to match the inclination and shape of the standard image data 20 with the inclination and shape of the radiation image data 12. As a result, it is possible to prevent errors of an inclination and a shape that do not result from a defect of the test object 11 which is a test target from occurring between the standard image data 20 and the radiation image data 12. Further, through the density correction process, it is possible to correct a density difference between a normal region of the radiation image data 12 and a corresponding region of the standard image data 20. As a result, it is possible to reduce a density difference that does not result from a defect of the test object 11 that is a test target to become almost zero between the standard image data 20 and the radiation image data 12.

As shown in FIG. 4 described above, the differential value detection unit 42 detects differential values of pixel values between the corresponding pixels of the radiation image data 12 input from the radiation image acquisition unit 40 and the standard image data 20 input from the standard image correction unit 41 for each pixel to obtain the differential value detection result 45 (step S6, corresponding to a differential value detection step in the invention). Further, the differential value detection unit 42 outputs the differential value detection result 45 to the radiation image storage unit 38 and the display control unit 43, respectively.

As shown in the above-described FIG. 5, the radiation image storage unit 38 stores the differential value detection result 45 input from the differential value detection unit 42 in a DICOM file of the corresponding radiation image data 12 as additional information (step S6).

The display control unit 43 first determines a region formed by pixels where the differential values are generated as the differential region 47 of the radiation image data 12 and the standard image data 20 on the basis of the differential value detection result 45 input from the differential value detection unit 42. Then, the display control unit 43 generates the superimposed image data 48 obtained by superimposing the differential region 47 on the radiation image data 12 input from the radiation image data 40, and causes the display unit 32 to display the superimposed image data 48 (see FIG. 6). Here, the display control unit 43 causes the display unit 32 to display the differential region 47 in the superimposed image data 48 so that positive and negative of the differential values in the differential region 47 can be determined by giving different colors to the differential region 47 where the differential values are positive and the differential region 47 where the differential values are negative (step S7, corresponding to a display control step in the invention).

The differential region 47 where the differential values are positive is a region having a possibility that a defect such as an air bubble is included in the test object 11. The differential region 47 where the differential values are negative is a region having a possibility that a defect such as an impurity is included in the test object 11. Since the type of a defect is changed according to the positive or negative of the differential values in the differential region 47, the inspector can rapidly and reliably recognize situations (types) of defects that are likely to be included in the test object 11 and distributions of the respective defects, on the basis of the differential region 47 in the superimposed image data 48 displayed on the display unit 32. Further, since the superimposed image data 48 obtained by superimposing the differential region 47 on the radiation image data 12 of the test object 11 is displayed, the inspector can easily recognize a position where the differential region 47 in the test object 11 is generated.

Here, in a case in which the differential region 47 in the superimposed image data 48 is displayed on the display unit 32, it is preferable to display the differential region 47 on the display unit 32 so that the magnitudes of absolute values of the differential values can be determined, for example, so that the display density of the differential region 47 is changed according to the sizes of the absolute values of the differential values. Thus, the inspector can easily specify the differential region 47 with large differential values and a high defect possibility. Further, even in a case in which a plurality of types of defects where the differential values are positive or a plurality of types of defects where the difference values are negative are present, in a case in which the sizes of the differential values are configured to be different from each other according to the types of defects, it is possible to specify the types of the defects by changing the display density.

A standard of differential values in determining a defect possibility of the differential region 47 is changed according to the type of the test object 11, a test period, a request of a customer, and the like, but in this embodiment, the differential value detection result 45 is stored in the radiation image storage unit 38 in association with the radiation image data 12. Even in a case in which the standard (threshold value) of the differential values in determining the defect possibility of the differential region 47 is changed, it is possible to determine the defect possibility of the differential region 47 according to a new standard with reference to the differential value detection result 45 stored in the radiation image storage unit 38, which will be described below in detail in a second embodiment. As a result, it is possible to specify the test object 11 with a defect possibility using the new criteria.

After the superimposed image data 48 is displayed, in a case in which the inspector performs a magnification display of the differential region 47 in the superimposed image data 48, the inspector selects the differential region 47 to be magnified and displayed using the keyboard 27, the mouse 28, or the like (step S8). The magnification display unit 50 receives the selection operation, generates the magnified image data 53 obtained by magnifying the selected differential region 47 in the superimposed image data 48, and causes the display unit 32 to display the magnified image data 53 together with the superimposed image data 48 (step S9, see FIG. 6). Further, the magnification display unit 50 displays the scale 53a indicating the dimension of the differential region 47 in the magnified image data 53. Thus, the inspector can recognize a detailed state and the size of the differential region 47, and thus, it is possible to easily determine whether the differential region 47 is a defect.

In a case in which the inspector performs a selective display of any one of the differential region 47 where the differential values are positive and the differential region 47 where the differential values are negative, the inspector performs a display instruction through the keyboard 27, the mouse 28, or the like (step S10). The selective display unit 51 receives the display instruction, and causes the display unit 32 to selectively display any one of the differential region 47 where the differential values are positive and the differential region 47 where the differential values are negative, as shown in FIGS. 7A and 7B (step S11). Thus, the inspector can easily recognize a distribution of the differential region 47 where the differential values are positive and a distribution of the differential region 47 where the differential values are negative, and thus, it is possible to easily recognize the distribution of the differential region 47 with a specific defect possibility.

Further, in a case in which the inspector directly observes a portion corresponding to the differential region 47 of the radiation image data 12, the inspector performs a display stop operation of the differential region 47 using the keyboard 27, the mouse 28, or the like to turn off the display of the differential region 47. Thus, the inspector can directly observe the portion corresponding to the differential region 47 of the radiation image 12, and thus, it is possible to determine whether the differential region 47 is a defect.

In a case in which the display of the superimposed image data 48 of the test object 11 that is a test target is continued, situations (types) of defects included in the test object 11 and distributions of the respective defects are confirmed by appropriately performing turning on or off the display of the magnified image data 53 or performing the selective display of any one of the differential region 47 where the differential values are positive and the differential region 47 where the differential values are negative (YES in step S12, and steps S7 to S11).

On the other hand, in a case in which the inspector switches a test object (NO in step S12 and Yes in step S13), the inspector re-specifies the radiation image data 12 of the test object 11 that is to be subjected to a test using the keyboard 27, the mouse 28, or the like. Thus, the processes from step S3 to step S12 are repeatedly executed, so that new superimposed image data 48 is displayed on the display unit 32.

Thereafter, the processes from step S3 to step S12 are repeatedly executed until the test is terminated (NO in step S13).

[Effects of Non-destructive Testing Apparatus According to First Embodiment]

In the above-described non-destructive testing apparatus 10 according to the first embodiment, since the differential region 47 of the radiation image data 12 of the test object 11 that is a test target and the standard image data 20 is displayed on the display unit 32 so that positive and negative of differential values in the differential region 47 can be determined, it is possible to rapidly and reliably recognize the situations (types) of defects that are likely to be included in the test object 11 and distributions of the respective defects.

[Configuration of Non-destructive Testing Apparatus According to Second Embodiment]

Next, a non-destructive testing apparatus according to a second embodiment of the invention will be described. In the non-destructive testing apparatus 10 in the first embodiment, the differential region 47 formed by pixels where differential values are generated is displayed on the display unit 32. On the other hand, in the non-destructive testing apparatus according to the second embodiment, a differential region 47 formed by pixels for which absolute values of differential values are larger than a threshold value defined by a predetermined test standard is displayed on the display unit 32.

Figure 9:
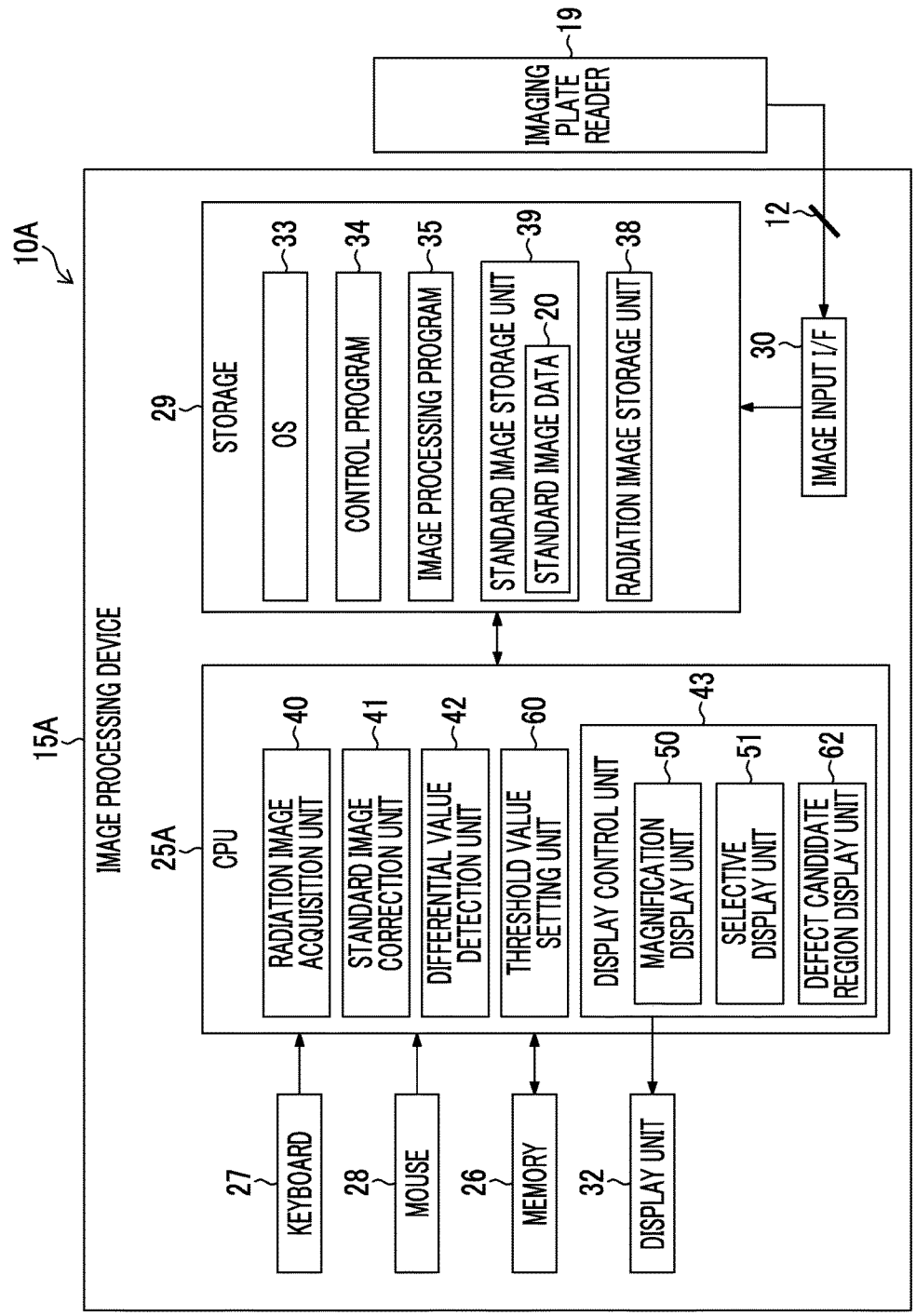
FIG. 9 is a functional block diagram of an image processing device that forms a non-destructive testing apparatus according to a second embodiment.

FIG. 9 is a functional block diagram of an image processing device 15A that forms a non-destructive testing apparatus 10A according to the second embodiment. As shown in FIG. 9, the non-destructive testing apparatus 10A according to the second embodiment has basically the same configuration as that of the non-destructive testing apparatus 10 in the first embodiment except that a CPU 25A of the image processing device 15A functions as a threshold value setting unit 60 in addition to the above-described radiation image acquisition unit 40, standard image correction unit 41, differential value detection unit 42 and display control unit 43, and that the display control unit 43 also functions as a defect candidate region display unit 62. Thus, the same reference numerals are given to the same functions and configurations as in the first embodiment, and description thereof will not be repeated.

The threshold value setting unit 60 corresponds to a threshold value change unit in the invention. The threshold value setting unit 60 sets a threshold value of absolute values of differential values for determining the differential region 47 as a defect candidate region with a high defect possibility. The threshold value is a value determined according to a test standard of a test object 11, which is determined in advance by a customer who uses the non-destructive testing apparatus 10A. The threshold value setting unit 60 receives an input of the threshold value through the keyboard 27, the mouse 28, or the like, and performs setting of the threshold value. Further, in a case in which the threshold value setting unit 60 receives an input of a new threshold value through the keyboard 27, the mouse 28, or the like, the threshold value setting unit 60 changes a previously set threshold value into the new threshold value.

Figure 10A:
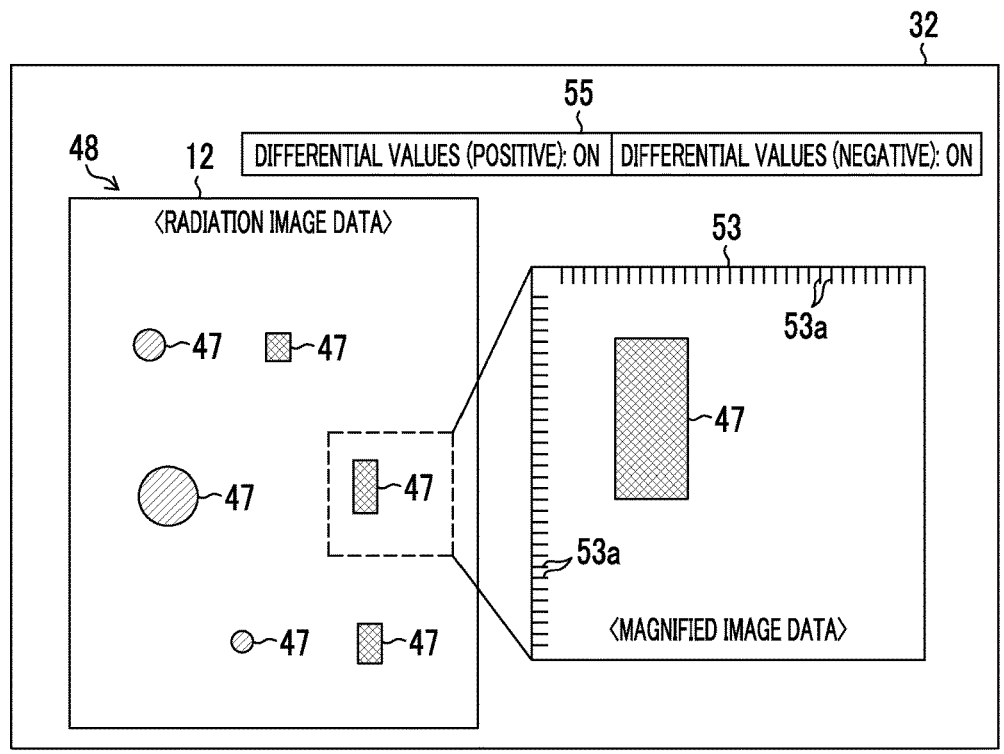
FIGS. 10A and 10B are diagrams illustrating display controls of differential regions in the second embodiment.
Figure 10B:
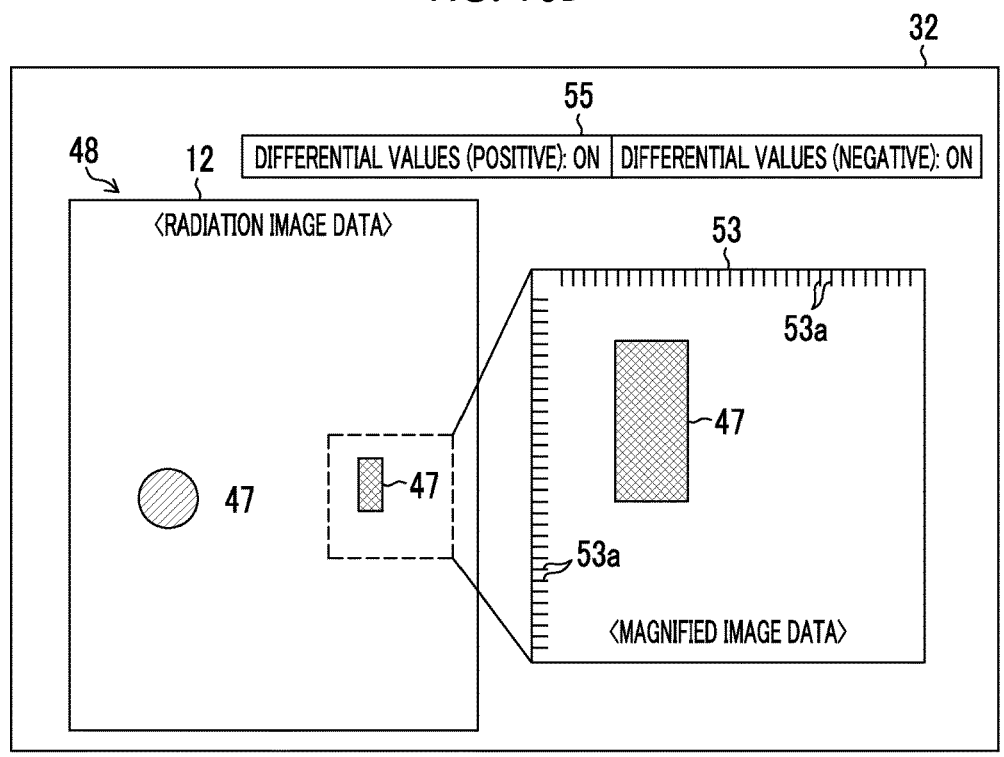

FIGS. 10A and 10B are diagrams illustrating display controls of differential regions 47 in the second embodiment. As shown in FIG. 10A, the display control unit 43 according to the second embodiment causes the display unit 32 to display a differential region 47 where differential values are generated in superimposed image data 48 so that positive and negative of the differential values in the differential region 47 can be determined, similar to the first embodiment.

In a case in which a display operation of a defect candidate region is performed through the keyboard 27, the mouse 28, or the like, the defect candidate region display unit 62 determines, with reference to a threshold value set by the threshold value setting unit 60, a differential region 47 where absolute values of differential values are equal to or greater than the threshold value in the differential region 47 on the basis of a differential value detection result 45 input from the differential value detection unit 42. Then, as shown in FIG. 10B, the defect candidate region display unit 62 causes the display unit 32 to display only the differential region 47 where the absolute values of the differential values are equal to or greater than the threshold value so that positive and negative of the differential values can be determined.

Further, in a case in which the threshold value is changed by the threshold value setting unit 60, the defect candidate region display unit 62 causes the display unit 32 to redisplay the differential region 47 where the absolute values of the differential values are equal to or greater than the threshold value after the change, on the basis of the previous radiation image data 12 and the differential value detection result 45 stored in the radiation image storage unit 38 so that positive and negative of the differential values can be determined, for each piece of radiation image data 12.

Figure 11A:
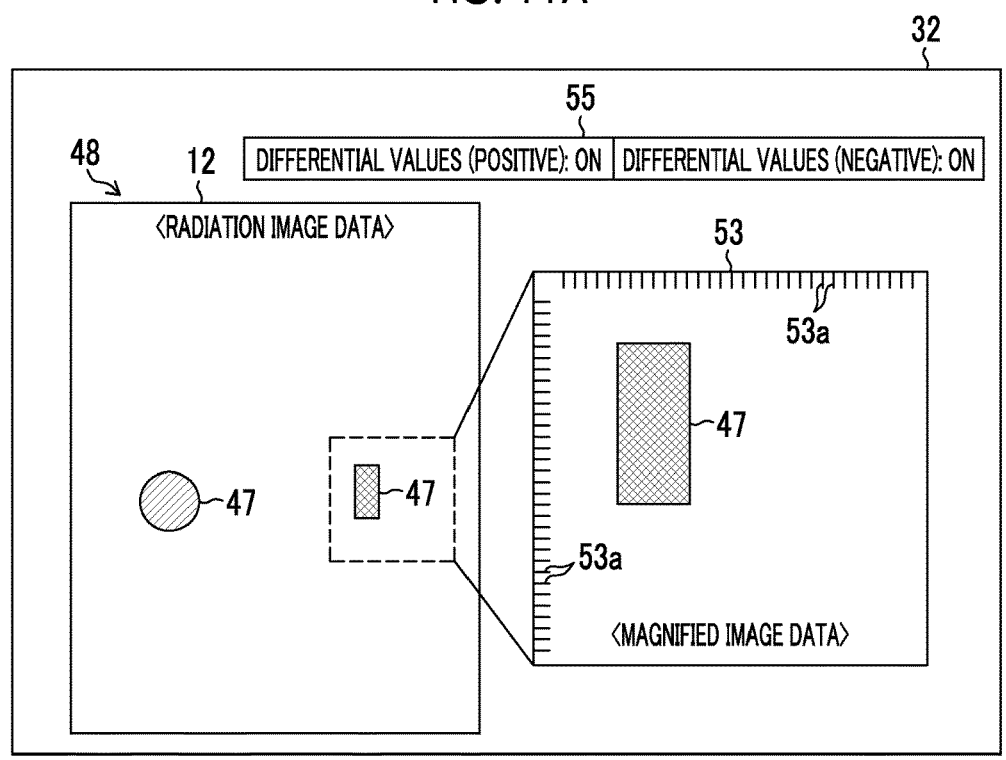
FIGS. 11A and 11B are diagrams illustrating display controls of differential regions with respect to previous radiation image data after a change of a threshold value.
Figure 11B:
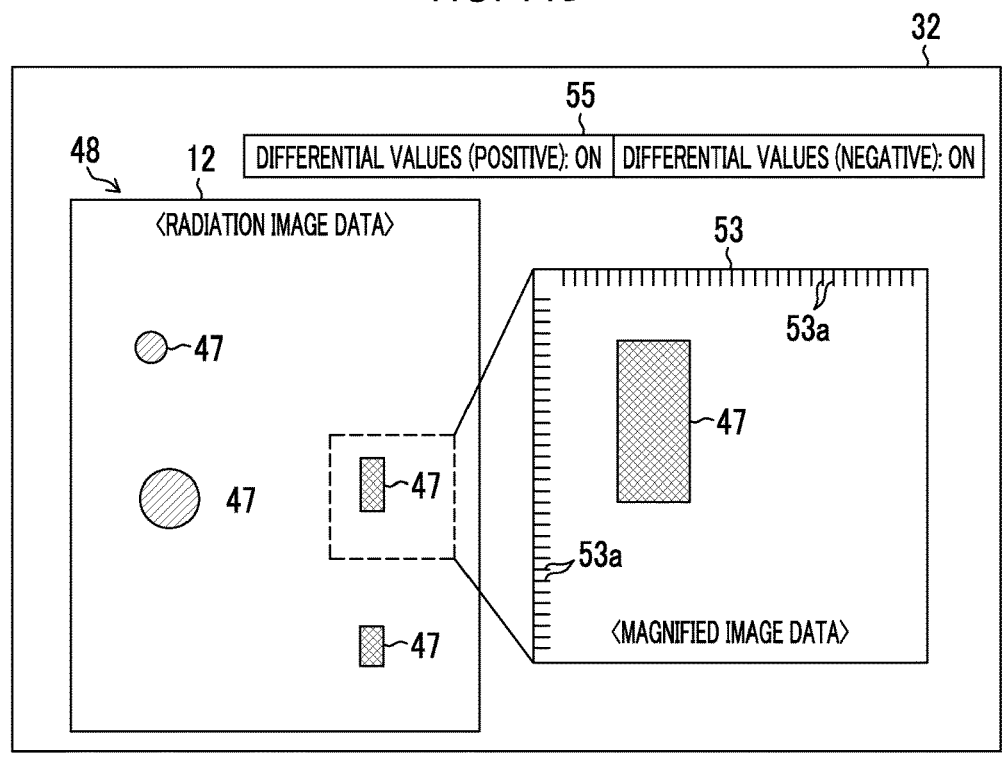

FIGS. 11A and 11B are diagrams illustrating display controls of the differential regions 47 with respect to the previous radiation image data 12 after change of the threshold value, in which FIG. 11A shows a state before change of the threshold value, and FIG. 11B shows a state after change of the threshold value. In the following description, it is assumed that the threshold value is changed to become low.

As shown in FIG. 9 and FIGS. 11A and 11B, after the threshold value is changed by the threshold value setting unit 60, in a case in which a redisplay instruction of a defect candidate region of the previous radiation image data 12 is input through the keyboard 27, the mouse 28, or the like, the defect candidate region display unit 62 reads corresponding radiation image data 12 and the differential value detection result 45 from the radiation image storage unit 38. Further, the defect candidate region display unit 62 determines a differential region 47 where absolute values of differential values are equal to or greater than the threshold value after change in the differential region 47 with reference to the threshold value after change set by the threshold value setting unit 60, on the basis of the differential value detection result 45 read from the radiation image storage unit 38.

Then, the defect candidate region display unit 62 generates new superimposed image data 48 obtained by superimposing the differential region 47 where the absolute values of the differential values are equal to or greater than the threshold value on the radiation image data 12 read from the radiation image storage unit 38, and causes the display unit 32 to display the superimposed image data 48. Further, the defect candidate region display unit 62 causes the display unit 32 to display the differential region 47 in the superimposed image data 48 so that positive and negative of the differential values in the differential region 47 can be determined. Thus, the differential region 47 where the absolute values of the differential values are equal to or greater than the threshold value after change is redisplayed on the display unit 32 so that the positive and negative of the differential values can be determined. In this embodiment, since the threshold value is changed to a low value, compared with the state before change of the threshold value shown in FIG. 11A, in the case of the state after change of the threshold value shown in FIG. 11B, the number of differential regions 47 displayed on the display unit 32 increases.

[Operation of Non-destructive Testing Apparatus According to Second Embodiment]

Figure 12:
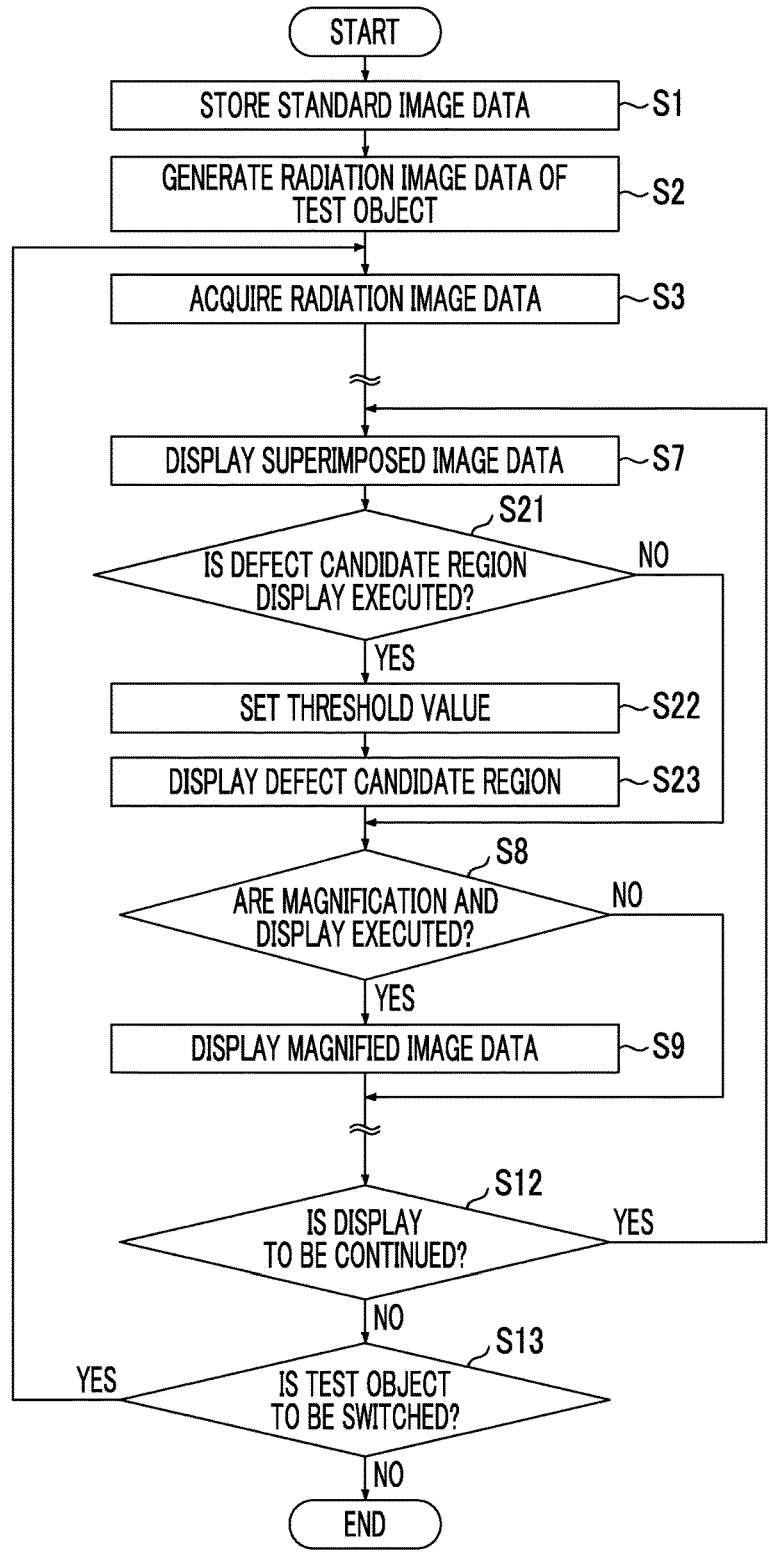
FIG. 12 is a flowchart illustrating a flow of a display process of a differential region in the non-destructive testing apparatus according to the second embodiment.

Next, an operation of the non-destructive testing apparatus 10A according to the second embodiment will be described with reference to FIG. 12. FIG. 12 is a flowchart illustrating a flow of a display process of the differential region 47 in the non-destructive testing apparatus 10A according to the second embodiment.

As shown in FIG. 12, since processes from step S1 to step S7 are basically the same as in the first embodiment shown in FIG. 8, detailed description will not be repeated. In a case in which the processes up to step S7 are terminated, as shown in FIG. 10A, the superimposed image data 48 is displayed on the display unit 32, and the entire differential region 47 in the superimposed image data 48 is displayed on the display unit 32 so that positive and negative of differential values can be determined.

In a case in which an inspector displays only a defect candidate region on the display unit 32 in the differential region 47, the inspector performs a display operation of the defect candidate region using the keyboard 27, the mouse 28, or the like (step S21). In this case, the threshold value setting unit 60 receives an input of a threshold value through the keyboard 27, the mouse 28, or the like, and performs setting of the threshold value (step S22). Further, a timing in a case in which the threshold value is input and set is not particularly limited as long as it is a stage before step S21.

The defect candidate region display unit 62 receives the display operation of the defect candidate region, and determines a differential region 47 where absolute values of differential values are equal to or greater than the threshold value in each differential region 47, with reference to the threshold value set by the threshold value setting unit 60, on the basis of the differential value detection result 45 input from the differential value detection unit 42. Then, as shown in FIG. 10B, the defect candidate region display unit 62 causes the display unit 32 to display only the differential region 47 where the absolute values of the differential values are equal to or greater than the threshold value as the defect candidate region so that positive and negative of the differential values can be determined (step S23).

Since subsequent processes (a magnification display or a selective display of the differential region 47) are basically the same as in the first embodiment shown in FIG. 8, detailed description thereof will not be repeated.

<Redisplay of Defect Candidate Region after Threshold Value Change>

Figure 13:
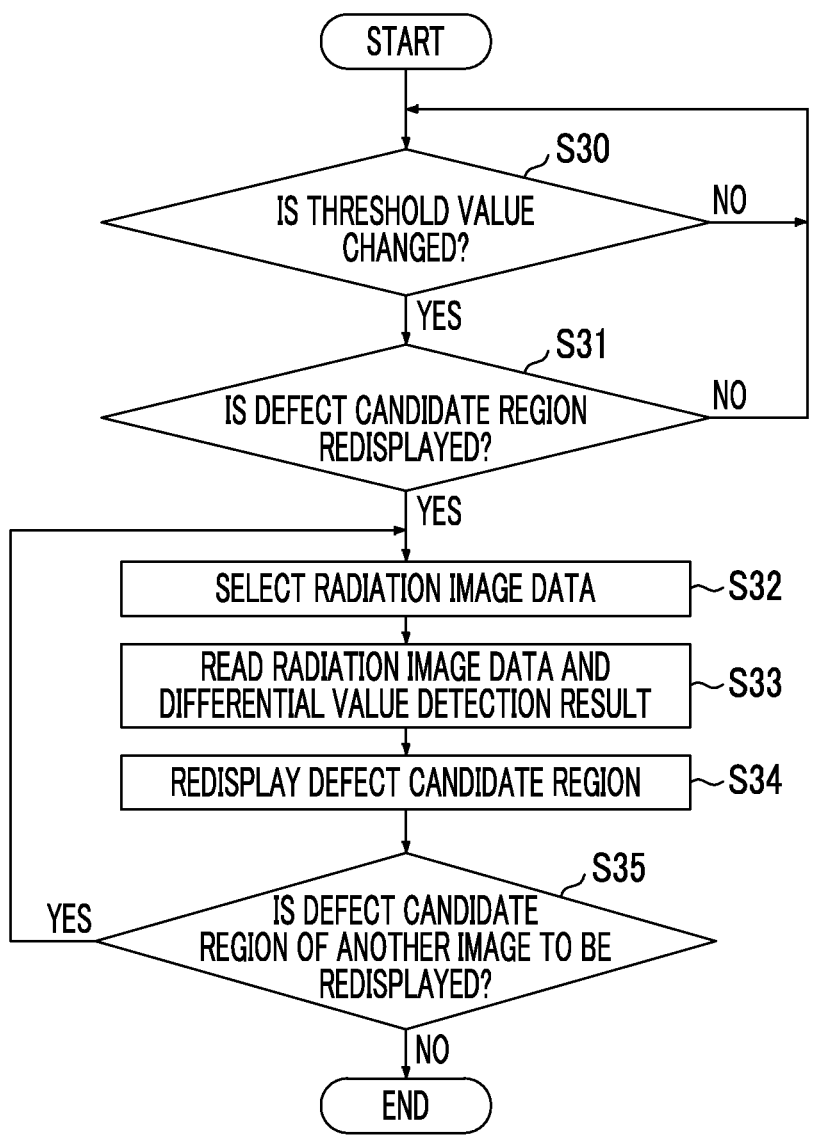
FIG. 13 is a flowchart illustrating a flow of a redisplay process of a differential region with respect to previous radiation image data in the non-destructive testing apparatus according to the second embodiment.

FIG. 13 is a flowchart illustrating a flow of a redisplay process of the differential region 47 (defect candidate region) with respect to the previous radiation image data 12 in the non-destructive testing apparatus 10A.

As shown in FIG. 13, in a case in which an inspector changes a threshold value that is a standard in determining a defect candidate region, the inspector performs input of a new threshold value through the keyboard 27, the mouse 28, or the like. The threshold value setting unit 60 receives the input of the threshold value, and changes the previously set threshold value into a new threshold value (step S30).

After change of the threshold value, in a case in which the inspector performs redisplay of the defect candidate region of the previous radiation image data 12, the inspector performs a redisplay operation of the defect candidate region using the keyboard 27, the mouse 28, or the like (step S31). Further, the inspector selects the previous radiation image data 12 for which the redisplay of the defect candidate region is to be performed using the keyboard 27, the mouse 28, or the like (step S32).

The defect candidate region display unit 62 receives the redisplay operation of the defect candidate region, and reads the selected previous radiation image data 12 and the differential value detection result 45 that is stored in associated with the radiation image data 12 from the radiation image storage unit 38, respectively (step S33).

Then, the defect candidate region display unit 62 determines a differential region 47 where absolute values of differential values are equal to or greater than the threshold value after change in the differential region 47, with reference to the threshold value after change set by the threshold value setting unit 60, on the basis of the differential value detection result 45 read from the radiation image storage unit 38. Further, the defect candidate region display unit 62 generates superimposed image data 48 obtained by superimposing the differential region 47 where the absolute values of the differential values are equal to or greater than the previous radiation image data 12 read from the radiation image storage unit 38, and causes the display unit 32 to display the superimposed image data 48.

Here, the defect candidate region display unit 62 causes the display unit 32 to display the differential region 47 in the superimposed image data 48 as the defect candidate region so that positive and negative of the differential values in the differential region 47 can be determined (step S34). Thus, the differential region 47 corresponding to the threshold value after change is redisplayed as the defect candidate region on the display unit 32. The magnification display and the selective display of the differential region 47 as described in the first embodiment may be performed as necessary.

In a case in which the inspector changes the previous radiation image data 12 for performing the redisplay of the differential region 47, the inspector selects another piece of radiation image data 12 stored in the radiation image storage unit 38 using the keyboard 27, the mouse 28, or the like (step S35). Further, by repeatedly executing the respective processes from the above-described step S32 to step S34, the differential region 47 corresponding to the threshold value after change is redisplayed as the defect candidate region on the display unit 32. Thereafter, until the test is terminated, the processes from step S32 to step S35 are repeatedly executed. Although not shown, in a case in which the threshold value is changed, the processes from the above-described step S30 to step S35 are repeatedly executed.

[Effects of Non-destructive Testing Apparatus According to Second Embodiment]

As described above, in the non-destructive testing apparatus 10A according to the second embodiment, it is possible to cause the display unit 32 to display the differential region 47 for which the absolute values of the differential values are larger than the threshold value defined by the predetermined test standard in the differential region 47, that is, only a defect candidate region with a high defect possibility so that positive and negative of the differential values can be determined. Thus, an inspector can easily specify the differential region 47 with a high defect possibility, and thus, it is possible to more rapidly and reliably recognize the situations (types) of defects that are likely to be included in the test object 11 and distributions of the respective defects. Further, even in a case in which a plurality of types of defects having positive differential values or a plurality of types of defects having negative differential values are present, in a case in which the sizes of the differential values are different from each other according to the types of the defects, by setting a threshold value, it is possible to cause the display unit 32 to display only the differential region 47 with a specific defect possibility.

Further, in the non-destructive testing apparatus 10A in the second embodiment, the differential value detection result 45 is stored in the radiation image storage unit 38 in association with the radiation image data 12. Thus, in the non-destructive testing apparatus 10A, even in a case in which a threshold value of differential values in determining a defect possibility of the differential region 47 is changed later, it is possible to cause the display unit 32 to redisplay the differential region 47 corresponding to the threshold value after change as a defect candidate region, with respect to previous radiation image data 12, on the basis of the previous differential value detection result 45 in the radiation image storage unit 38. As a result, in a case in which the threshold value is changed, it is possible to easily recognize the differential region 47 with a high defect possibility using the threshold value after change as a standard.

[Configuration of Non-destructive Testing Apparatus According to Third Embodiment]

Next, a non-destructive testing apparatus according to a third embodiment of the invention will be described. In the non-destructive testing apparatus 10 according to the first embodiment, the geometric deformation process or the density correction process is performed with respect to the reference image data 20, and thus, errors of an inclination and a shape between the standard image data 20 and the radiation image data 12 and a density difference therebetween are corrected, but there is a concern that a density difference due to variation in the above-mentioned imaging conditions occurs even between the plurality of pieces of radiation image data 12. In this case, a density difference occurs in the plurality of pieces of superimposed image data 48 generated on the basis of the plurality of pieces of radiation image data 12. As a result, it is necessary for an inspector to determine whether the density difference between the plurality of pieces of superimposed image data 48 results from a defect or from variation in the imaging conditions, and thus, it takes time for the test.

Accordingly, in the non-destructive testing apparatus according to the third embodiment, a process for correcting a density difference due to a variation in imaging conditions is performed with respect to a plurality of pieces of radiation image data 12 acquired by the imaging unit 14 (see FIG. 1).

Figure 14:
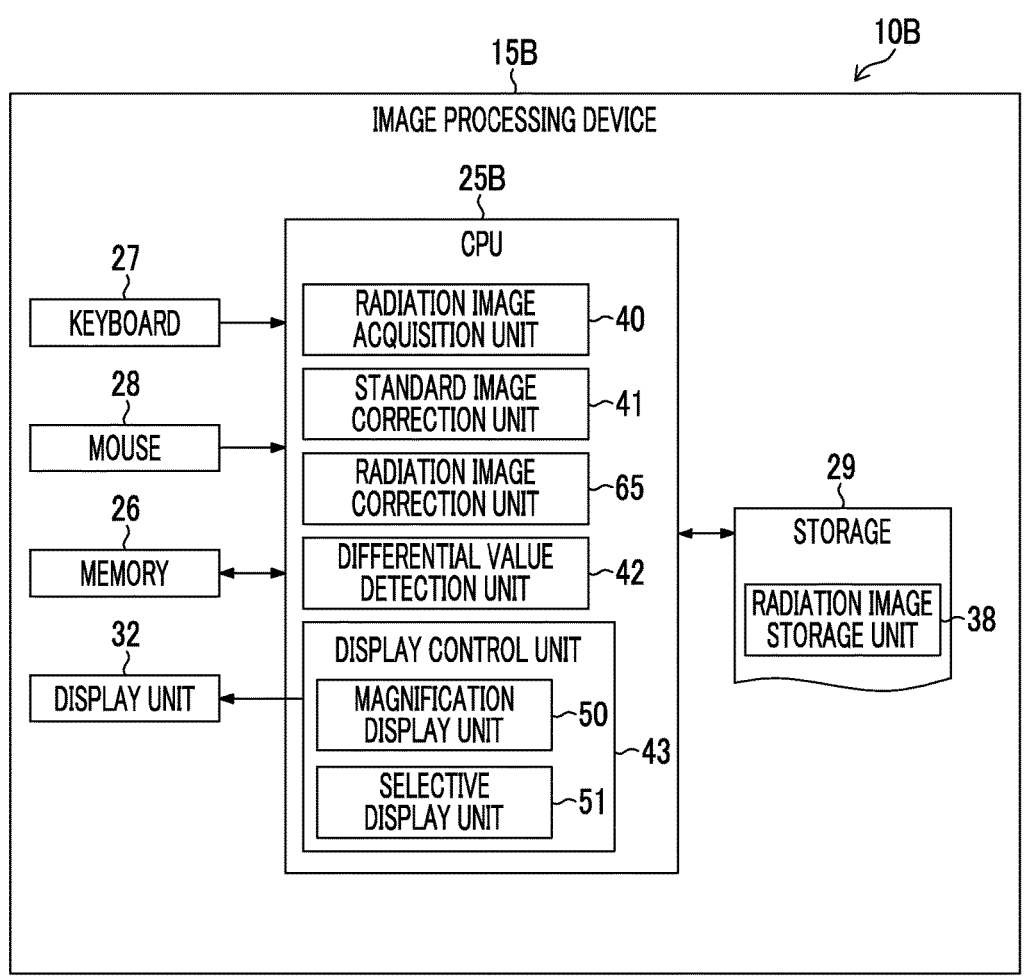
FIG. 14 is a block diagram illustrating an electric configuration of an image processing device of a non-destructive testing apparatus according to a third embodiment.

FIG. 14 is a block diagram illustrating an electric configuration of an image processing device 15B of a non-destructive testing apparatus 10B according to the third embodiment. As shown in FIG. 14, the non-destructive testing apparatus 10B according to the third embodiment has basically the same configuration as that of the non-destructive testing apparatus 10 in the first embodiment except that a CPU 25B of the image processing device 15B functions as a radiation image correction unit 65 in addition to the above-described radiation image acquisition unit 40, standard image correction unit 41, differential value detection unit 42 and display control unit 43. Thus, the same reference numerals are given to the same functions and configurations as in the first embodiment, and description thereof will not be repeated.

Figure 15:
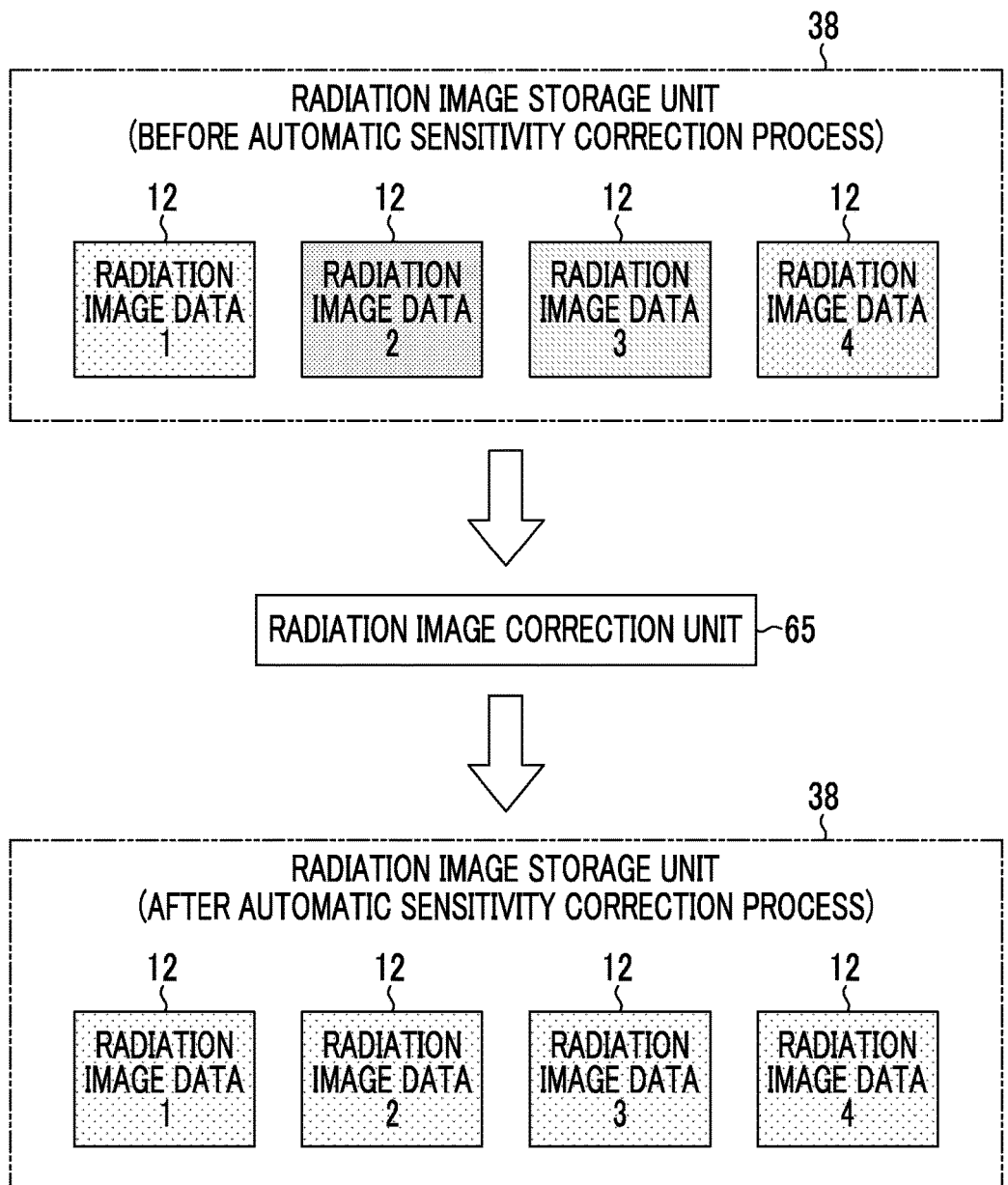
FIG. 15 is a diagram illustrating image processing of radiation image data in a radiation image correction unit.

FIG. 15 is a diagram illustrating image processing of radiation image data 12 in the radiation image correction unit 65. As shown in FIG. 15, the radiation image correction unit 65 corresponds to a third image correction unit in the invention. The radiation image correction unit 65 performs a process of correcting a density difference due to variation in imaging conditions, with respect to the plurality of pieces of radiation image data 12 acquired by the imaging unit 14, at least before processing in the above-described standard image correction unit 41. Specifically, the radiation image correction unit 65 performs an automatic sensitivity correction process [an exposure data recognizer (EDR) process] with respect to the above-described plurality of pieces of radiation image data 12.

The automatic sensitivity correction process [exposure data recognizer (EDR) process] is a process of correcting (normalizing density or contrast) a density difference or the like between a plurality of pieces of radiation image data due to variation in imaging conditions, which is a known technique (for example, see JP2012-45331A or JP2013-

236961A). Hereinafter, an example of the automatic sensitivity correction process [exposure data recognizer (EDR)] will be described.

The radiation image correction unit 65 reads the plurality of pieces of radiation image data 12 with respect to the same type of the subject object 11 stored in the radiation image storage unit 38, respectively, and detects a histogram indicating a relationship between pixels that form the radiation image data 12 and pixel values thereof for each piece of the radiation image data 12. Further, the radiation image correction unit 65 analyzes the histogram for each piece of the radiation image data 12 to determine a plurality of points of interest (points for matching densities between the respective pieces of radiation image data 12) in respective pieces of radiation image data 12. The points of interest may be determined by a manual operation of an inspector from the histogram for each piece of radiation image data 12.

Then, the radiation image correction unit 65 performs a density correction process with respect to each piece of radiation image data 12 so that the densities of the points of interest of respective pieces of radiation image data 12 become equal to each other (for example, become a predetermined standard density). Thus, the points of interest of the respective pieces of radiation image data 12 are corrected to have the same density, and the density of a region other than the points of interest is corrected to have a relative density with respect to the density of the points of interest. Thus, the density difference due to the variation in the imaging conditions with respect to the radiation image data 12 is corrected.

The above-described method of the automatic sensitivity correction process is an example of the automatic sensitivity correction process (EDR process), and various methods capable of correcting a density difference between a plurality of pieces of radiation image data 12 such as known other automatic sensitivity correction methods may be used.

[Operation of Non-destructive Testing Apparatus According to Third Embodiment]

Next, an operation of the non-destructive testing apparatus 10B according to the third embodiment will be described with reference to FIG. 16. FIG. 16 is a flowchart illustrating a flow of a display process of the differential region 47 in the non-destructive testing apparatus 10B, particularly, the automatic sensitivity correction process.

As shown in FIG. 16, since processes up to step S2 are basically the same as in the first embodiment shown in FIG. 8, detailed description thereof will not be repeated. In a case in which the processes up to step S2 are terminated, the radiation image data 12 with respect to all the test objects 11 that are test targets is acquired, and is stored in the radiation image storage unit 38.

In a case in which recording of the radiation image data 12 is terminated, the radiation image correction unit 65 reads the plurality of pieces of radiation image data 12 with respect to the same type of the subject objects 11 stored in the radiation image storage unit 38, respectively, and performs the above-described automatic sensitivity correction process (EDR process) (step S2A). Thus, a density difference between the plurality of pieces of radiation image data due to variation in imaging conditions is corrected. The radiation image data 12 after the automatic sensitivity correction process is stored again in the radiation image storage unit 38.

Since processes after step S3 are basically the same as in the first embodiment shown in FIG. 8, detailed description thereof will not be repeated. Further, as described in the second embodiment, only a differential region 47 which is a defect candidate region in the plurality of differential regions 47 may be displayed (see FIGS. 12 and 13).

[Effects of Non-destructive Testing Apparatus According to Third Embodiment]

As described above, since the non-destructive testing apparatus 10B according to the third embodiment performs a process of correcting a density difference due to variation in imaging conditions with respect to the plurality of pieces of radiation image data 12, a density difference between the plurality of pieces of superimposed image data 48 respectively generated on the basis of the plurality of pieces of radiation image data 12 is suppressed (reduced). As a result, an inspector does not need to determine whether the density difference between the plurality of pieces of superimposed image data 48 is caused by a defect or caused by variation in imaging conditions, and thus, it is possible to shorten time necessary for the test.

[Others]

In the above-described respective embodiments, the differential region 47 is displayed on the display unit 32 so that positive and negative of differential values in the differential region 47 can be determined by giving different colors to the differential region 47 where the differential values are positive and the differential region 47 where the differential values are negative, respectively, but the invention is not limited thereto. For example, various display methods capable of determining the positive and negative of the differential values in the differential regions 47, such as a method of changing the density (brightness) of the differential region 47 in display according to the positive and negative of the differential values, a method of providing a display frame that surrounds the differential regions 47 and changing a display mode of the display frame according to the positive or negative of the differential values, or a method of performing displays indicating the positive and negative of the differential regions 47, may be performed.

In the above-described respective embodiments, after the radiation image data 12 of all the test objects 11 which are test targets is acquired, the superimposed image data 48 or the differential region 47 corresponding to the radiation image data 12 specified by an inspector is displayed, but the acquisition of the radiation image data 12 of the test object 11 and the display of the superimposed image data 48 or the differential region 47 may be alternately repeated. In the third embodiment, similarly, by determining positions of points of interest in a histogram of the radiation image data 12 in advance, it is possible to individually perform an automatic sensitivity correction process with respect to the radiation image data 12 whenever the radiation image data 12 is acquired.

In the above-described respective embodiment, values obtained by subtracting "pixel values of pixels of the standard image data 20" from "pixel values of pixels of the radiation image data 12" are used as differential values, but values obtained by subtracting "pixel values of pixels of the radiation image data 12" from "pixel values of pixels of the standard image data 20" may be used as differential values. In this case, contrary to the above-described respective embodiments, the differential region 47 where differential values are positive is a region with a possibility that there is a defect such as an impurity in the test object 11, and the differential region 47 where differential values are negative is a region with a possibility that a defect such as an air bubble (also referred to as a "pore") is included in the test object 11.

In the above-described respective embodiments, the superimposed image data 48 obtained by superimposing the differential region 47 on the radiation image data 12 is displayed on the display unit 32, but only the differential region 47 may be displayed on the display unit 32. In this case, the radiation image data 12 may not be stored.

In the above-described respective embodiments, an example in which the radiation image data 12 is data on a transmission image of radiation that transmitted a test object has been described, but the invention may be applied to a case where radiation reflection image data obtained by imaging radiation reflected by a test object instead of the radiation transmission image data is acquired. Further, in the above-described respective embodiments, an example in which X-rays are used as radiation has been described, but the invention may be applied to a case where radiation other than X-rays is used.

In the above-described respective embodiments, an example in which an industrial product, an industrial facility or the like is the test object 11 has been described, but the invention may be applied to various image processing devices capable of acquiring the radiation image data 12 on various test objects (for example, a pipe line joint or the like) except for human beings.

In the above-described respective embodiments, a non-destructive testing apparatus that includes the imaging unit 14 and the image processing device 15, 15A, or 15B has been described as an example, but the image processing device according to the invention may include only the above-described image processing device 15, 15A, or 15B. That is, the invention may also be applied to an image processing device such as a personal computer or various arithmetic processing devices, which acquires the radiation image data 12 that is separately obtained through a recording medium such as a memory card or a communication network and displays the differential region 47 so that positive and negative of differential values can be determined, on the basis of the radiation image data 12.

As a measurement device described in the above-described embodiments, a program for causing a computer to function (the above-described image processing program 35, or the like) may be recorded on a compact disc read only memory (CD-ROM), a magnetic disc, a computer-readable medium (tangible non-transitory information storage medium), and may be provided through an information storage medium. Instead of a configuration in which the program is provided in a state of being stored in such an information storage medium, a program signal may be provided as a download service using a communication network such as the Internet.

EXPLANATION OF REFERENCES 10, 10A, 10B: non-destructive testing apparatus
11: test object
12: radiation image data
14: imaging unit
15, 15A, 15B: image processing device
17: radiation source
19: imaging plate reader
20: standard image data
38: radiation image storage unit
39: standard image storage unit
40: radiation image acquisition unit
41: standard image correction unit
42: differential value detection unit
43: display control unit
45: differential value detection unit
47: differential region
48: superimposed image data
53: magnified image data
60: threshold value setting unit
65: radiation image correction unit

What is claimed is:

1. An image processing device comprising:
a processor configured to
acquired a radiation image obtained by imaging a test object irradiated with radiation which transmitted the test object, wherein the test object is one of an industrial product and an industrial facility;
a standard image storage that stores a standard image which is a normal radiation image of the test object imaged under the same imaging condition as in the radiation image acquired by the processor;
the processor further configured to
detect differential values of pixel values between corresponding pixels of the radiation image acquired by the processor and the standard image stored in the standard image storage; and
cause a display unit to display a differential region between the radiation image and the standard image so that positive and negative of the differential values in the differential region can be determined on the basis of a detection result of the processor, and
wherein the radiation image is obtained by imaging the test object disposed between a radiation source and an imaging plate, and
wherein the imaging condition includes at least a distance between the radiation source and the test object, an intensity and an incident angle of radiation emitted to the test object from the radiation source, a geometrical position of the test object indicating a relative position or a posture of the test object with respect to the radiation source or the imaging plate, the kind or the shape of the imaging plate.

2. The image processing device according to claim 1, wherein the processor is capable of causing the display unit to selectively display any one of the differential region where the differential values are positive and the differential region where the differential values are negative.

3. The image processing device according to claim 1, wherein the processor causes the display unit to display the differential region where absolute values of the differential values are equal to or greater than a predetermined threshold value so that the positive and negative of the differential values can be determined, on the basis of the detection result of the processor.

4. The image processing device according to claim 2, wherein the processor causes the display unit to display the differential region where absolute values of the differential values are equal to or greater than a predetermined threshold value so that the positive and negative of the differential values can be determined, on the basis of the detection result of the processor.

5. The image processing device according to claim 3, further comprising:
a detection result storage that stores the detection result of the differential values detected by the processor for each radiation image; and
the processor further configured to change the threshold value,
wherein the processor causes, in a case in which the threshold value is changed by the processor, the display unit to display the differential region where the absolute values of the differential values are equal to or greater than the threshold value after the change so that the positive and negative of the differential values can be determined, on the basis of the detection result of the differential values stored in the detection result storage, for each radiation image.

6. The image processing device according to claim 4, further comprising:
a detection result storage unit that stores the detection result of the differential values detected by the processor for each radiation image; and
the processor further configured to change the threshold value,
wherein the processor further configured to change causes, in a case in which the threshold value is changed by the processor, the display unit to display the differential region where the absolute values of the differential values are equal to or greater than the threshold value after the change so that the positive and negative of the differential values can be determined, on the basis of the detection result of the differential values stored in the detection result storage, for each radiation image.

7. The image processing device according to claim 1, further comprising:
a radiation image storage that stores the radiation image; and
the processor further configured to store the detection result of the differential values detected by the processor in the radiation image storage in association with the radiation image.

8. The image processing device according to claim 2, further comprising:
a radiation image storage that stores the radiation image; and
the processor further configured to store the detection result of the differential values detected by the processor in the radiation image storage in association with the radiation image.

9. The image processing device according to claim 1, wherein the processor performs, with respect to the standard image stored in the standard image storage, a process of correcting a density difference between the standard image and the radiation image before detection of the differential values in the processor.

10. The image processing device according to claim 2, wherein the processor performs, with respect to the standard image stored in the standard image storage, a process of correcting a density difference between the standard image and the radiation image before detection of the differential values in the processor.

11. The image processing device according to claim 1, wherein the processor performs, with respect to the standard image stored in the standard image storage, a process of correcting to match an inclination and a shape of the standard image with an inclination and a shape of the radiation image by detecting a corresponding point and performing geometric deformation, before detection of the differential values in the processor.

12. The image processing device according to claim 2, wherein the processor performs, with respect to the standard image stored in the standard image storage, a process of correcting to match an inclination and a shape of the standard image with an inclination and a shape of the radiation image by detecting a corresponding point and performing geometric deformation, before detection of the differential values in the processor.

13. The image processing device according to claim 1, wherein the processor performs, with respect to a plurality of the radiation images acquired by the processor, a process of correcting a density difference due to variation in the imaging condition for each radiation image, wherein the processor detects differential values of pixel values between corresponding pixels of the radiation image corrected by the processor and the standard image for each radiation image.

14. The image processing device according to claim 2, wherein the processor performs, with respect to a plurality of the radiation images acquired by the processor, a process of correcting a density difference due to variation in the imaging condition for each radiation image, wherein the processor detects differential values of pixel values between corresponding pixels of the radiation image corrected by the processor and the standard image for each radiation image.

15. The image processing device according to claim 1, wherein the processor causes the display unit to display a superimposed image obtained by superimposing the differential region on the radiation image.

16. The image processing device according to claim 2, wherein the processor causes the display unit to display a superimposed image obtained by superimposing the differential region on the radiation image.

17. The image processing device according to claim 15, wherein the processor causes the display unit to display a magnified image obtained by magnifying the differential region in the superimposed image together with the superimposed image.

18. The image processing device according to claim 1, wherein the processor gives different colors to the differential region where the differential values are positive and the differential region where the differential values are negative, respectively, and causes the display unit to display the result.

19. The image processing device according to claim 1, wherein the normal radiation image of the test object is an image wherein at least one of bubbles, impurities and scars included in the test object do not exceed a predetermined threshold.

20. An image processing method comprising:
a radiation image acquisition step of acquiring a radiation image obtained by imaging a test object irradiated with radiation which transmitted the test object, wherein the test object is one of an industrial product and an industrial facility;
a standard image storage step of storing a standard image which is a normal radiation image of the test object imaged under the same imaging condition as in the radiation image acquired in the radiation image acquisition step, in a standard image storage;
a differential value detection step of detecting differential values of pixel values between corresponding pixels of the radiation image acquired in the radiation image acquisition step and the standard image stored in the standard image storage; and
a display control step of causing a display unit to display a differential region between the radiation image and the standard image so that positive and negative of the differential values in the differential region can be determined on the basis of a detection result in the differential value detection step, and wherein the radiation image is obtained by imaging the test object disposed between a radiation source and an imaging plate, and wherein the imaging condition includes at least a distance between the radiation source and the test object, an intensity and an incident angle of radiation emitted to the test object from the radiation source, a geometrical position of the test object indicating a relative position or a posture of the test object with respect to the radiation source or the imaging plate, the kind or the shape of the imaging plate.

21. A non-transitory computer readable recording medium storing a program that causes a computer of an image processing device to function as:

a radiation image acquisition unit that acquires, using an imaging unit that images a test object irradiated with radiation which transmitted the test object, a radiation image of the test object, wherein the test object is one of an industrial product and an industrial facility;

a differential value detection unit that detects differential values of pixel values between corresponding pixels of the radiation image acquired by the radiation image acquisition unit and a standard image which is a normal radiation image of the test object imaged under the same imaging condition as in the radiation image acquired by the radiation image acquisition unit; and a display control unit that causes a display unit to display a differential region between the radiation image and the standard image so that positive and negative of the differential values in the differential region can be determined on the basis of a detection result of the differential value detection unit, and wherein the radiation image is obtained by imaging the test object disposed between a radiation source and an imaging plate, and wherein the imaging condition includes at least a distance between the radiation source and the test object, an intensity and an incident angle of radiation emitted to the test object from the radiation source, a geometrical position of the test object indicating a relative position or a posture of the test object with respect to the radiation source or the imaging plate, the kind or the shape of the imaging plate.

* * * * *